United States Patent
Boronkay et al.

(10) Patent No.: US 10,045,835 B2
(45) Date of Patent: Aug. 14, 2018

(54) VARIABLE DIRECTION TOOTH ATTACHMENTS

(71) Applicant: ALIGN TECHNOLOGY, INC., San Jose, CA (US)

(72) Inventors: Allen Boronkay, San Jose, CA (US); Tzishing Jesse Lim, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/046,193

(22) Filed: Feb. 17, 2016

(65) Prior Publication Data

US 2017/0231722 A1     Aug. 17, 2017

(51) Int. Cl.
| A61C 3/00 | (2006.01) |
| A61C 7/08 | (2006.01) |
| A61C 7/00 | (2006.01) |
| A61C 7/14 | (2006.01) |

(52) U.S. Cl.
CPC .............. *A61C 7/08* (2013.01); *A61C 7/002* (2013.01); *A61C 7/14* (2013.01)

(58) Field of Classification Search
CPC .............. A61C 7/08; A61C 7/002; A61C 7/14
USPC ........................................................ 433/6–8
See application file for complete search history.

(56) References Cited

U.S. PATENT DOCUMENTS

| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23,1980, Los ngeles, CA, p. 195.

(Continued)

*Primary Examiner* — Cris L Rodriguez
*Assistant Examiner* — Matthew Saunders
(74) *Attorney, Agent, or Firm* — Wilson Sonsini Goodrich & Rosati

(57) ABSTRACT

Tooth attachments are provided comprising one or more convex surfaces for engagement by a surface of an orthodontic appliance. Polymeric shell appliances are provided in which the polymeric shell appliances are configured to provide one or more activation forces to facilitate tooth movement. The polymeric shell appliances may comprise one or more tooth receiving cavities. The polymeric shell appliances may further comprise an engagement portion with a surface configured to engage a convex attachment surface in order to apply a tooth moving force.

10 Claims, 18 Drawing Sheets

(56) References Cited

U.S. PATENT DOCUMENTS

| | | |
|---|---|---|
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,820,368 A | 10/1998 | Wolk |
| 5,823,778 A | 10/1998 | Schmitt |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,334,772 B1 | 1/2002 | Taub et al. |
| 6,350,120 B1 | 2/2002 | Sachdeva et al. |
| 6,382,975 B1 | 5/2002 | Poirier |
| 6,390,812 B1 | 5/2002 | Chishti et al. |
| 6,398,548 B1 | 6/2002 | Muhammad et al. |
| 6,402,707 B1 | 6/2002 | Ernst |
| 6,482,298 B1 | 11/2002 | Bhatnagar |
| 6,485,298 B2 | 11/2002 | Chishti et al. |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,629,840 B2 | 10/2003 | Chishti et al. |
| 6,695,613 B2 | 2/2004 | Taub et al. |
| 6,705,861 B2 | 3/2004 | Chishti et al. |
| 6,705,863 B2 | 3/2004 | Phan et al. |
| 6,722,880 B2 | 4/2004 | Chishti et al. |
| 6,830,450 B2 | 12/2004 | Knopp et al. |
| 6,976,840 B2 | 12/2005 | Taub et al. |
| 7,056,115 B2 | 6/2006 | Phan et al. |
| 7,059,850 B1 | 6/2006 | Phan et al. |
| 7,063,533 B2 | 6/2006 | Phan et al. |
| 7,125,248 B2 | 10/2006 | Phan et al. |

(56) References Cited

U.S. PATENT DOCUMENTS

| | | | |
|---|---|---|---|
| 7,147,464 B2 | 12/2006 | Taub et al. | |
| 7,507,088 B2 | 3/2009 | Taub et al. | |
| 7,556,497 B2 | 7/2009 | Taub et al. | |
| 7,600,999 B2 | 10/2009 | Knopp | |
| 7,658,610 B2 | 2/2010 | Knopp | |
| 7,771,195 B2 | 8/2010 | Knopp et al. | |
| 7,841,858 B2 | 11/2010 | Knopp et al. | |
| 7,901,207 B2 | 3/2011 | Knopp et al. | |
| 8,401,686 B2 | 3/2013 | Moss et al. | |
| 8,496,473 B2 | 7/2013 | Phan et al. | |
| 8,562,337 B2 | 10/2013 | Kuo et al. | |
| 8,708,697 B2 | 4/2014 | Li et al. | |
| 8,734,149 B2 | 5/2014 | Phan et al. | |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0198911 A1* | 10/2003 | Knopp | A61C 7/00 433/6 |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2009/0191502 A1* | 7/2009 | Cao | A61C 7/08 433/24 |
| 2010/0138025 A1 | 6/2010 | Morton et al. | |
| 2011/0123944 A1 | 5/2011 | Knopp et al. | |
| 2011/0269092 A1 | 11/2011 | Kuo et al. | |
| 2013/0204599 A1 | 8/2013 | Matov et al. | |
| 2014/0193767 A1 | 7/2014 | Li et al. | |
| 2014/0322662 A1 | 10/2014 | Phan et al. | |
| 2014/0363779 A1 | 12/2014 | Kopelman | |
| 2015/0216627 A1 | 8/2015 | Kopelman | |
| 2015/0265376 A1 | 9/2015 | Kopelman | |
| 2015/0366637 A1 | 12/2015 | Kopelman et al. | |
| 2015/0366638 A1 | 12/2015 | Kopelman et al. | |
| 2016/0051341 A1 | 2/2016 | Webber | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl Heinz Holme and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Operation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

(56) References Cited

OTHER PUBLICATIONS

Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatorry, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolinggampproduction/november011996/simulatingstressputonfa. . .>.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.

(56) References Cited

OTHER PUBLICATIONS

Kesling, Coordinating the Predetermined Pattern and Tooth Positioner with Conventional Treatment, Am. J. Orthod. Oral Surg. (1946) 32:285-293.

Kleeman et al., The Speed Positioner, J. Clin. Orthod. (1996) 30:673-680.

Kochanek, "Interpolating Splines with Local Tension, Continuity and Bias Control," Computer Graphics, 18(3):33-41 (Jul. 1984). Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy as One, Two, Three," AOA/Pro Corner, vol. 11, No. 1, 2 pages (2002).

Mormann et al., "Marginale Adaptation von adhasuven Porzellaninlays in vitro," Separatdruck aus:Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

Procera Research Projects, "PROCERA Research Projects 1993—Abstract Collection," pp. 3-7 28 (1993).

Proffit et al., Contemporary Orthodontics, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <http://www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow et al. "CAD/CAM for Dental Restorations—Some of the Curious Challenges,".IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Surg., 114:438-442 (Apr. 1988).

Schroeder et al., Eds. The Visual Toolkit, Prentice Hall PTR, New Jersey (1998) Chapters 6, 8 & 9, (pp. 153-210,309-354, and 355-428, respectively).

Shilliday, (1971). Minimizing finishing problems with the mini-positioner, Am. J. Orthod. 59:596-599.

Siemens, "CEREC—Computer-Reconstruction," High Tech in der Zahnmedizin, 14 pages total (2004).

Sinclair, "The Readers' Corner," J. Clin. Orthod., 26(6):369-372 (Jun. 1992).

Sirona Dental Systems GmbH, CEREC 3D, Manuel utiiisateur, Version 2.0X (in French), 2003,114 pages total.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice is Clear: Red, White & Blue ... The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).

The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).

The Choice is Clear: Red, White & Blue . . . The Simple, Affordable, No-Braces Treatment, Allesee Orthodontic Appliances-Pro Lab product information, 6 pages (2003).

The Red, White & Blue Way to Improve Your Smile! Allesee Orthodontic Appliances-Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

(56) References Cited

OTHER PUBLICATIONS

U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

\* cited by examiner

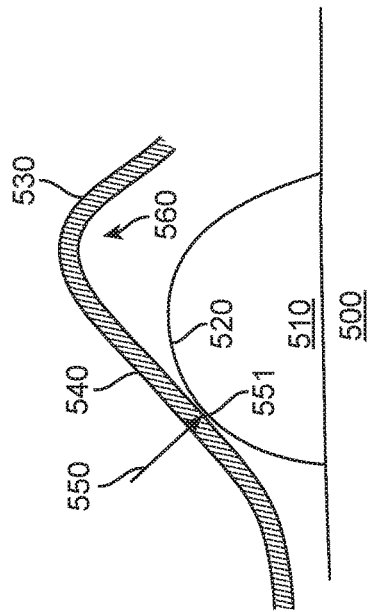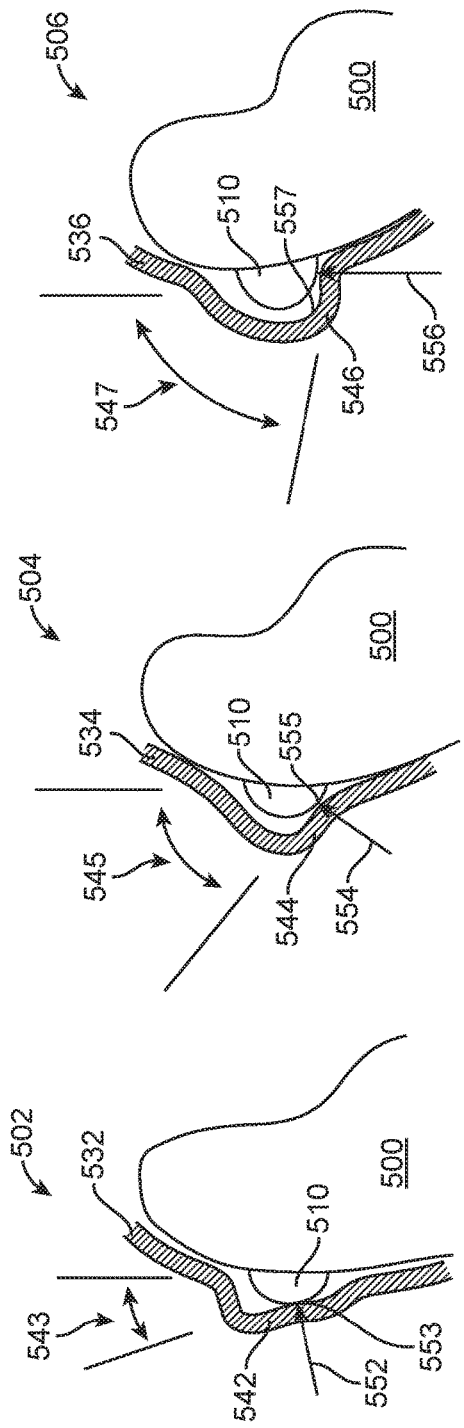
FIG. 5A
FIG. 5B

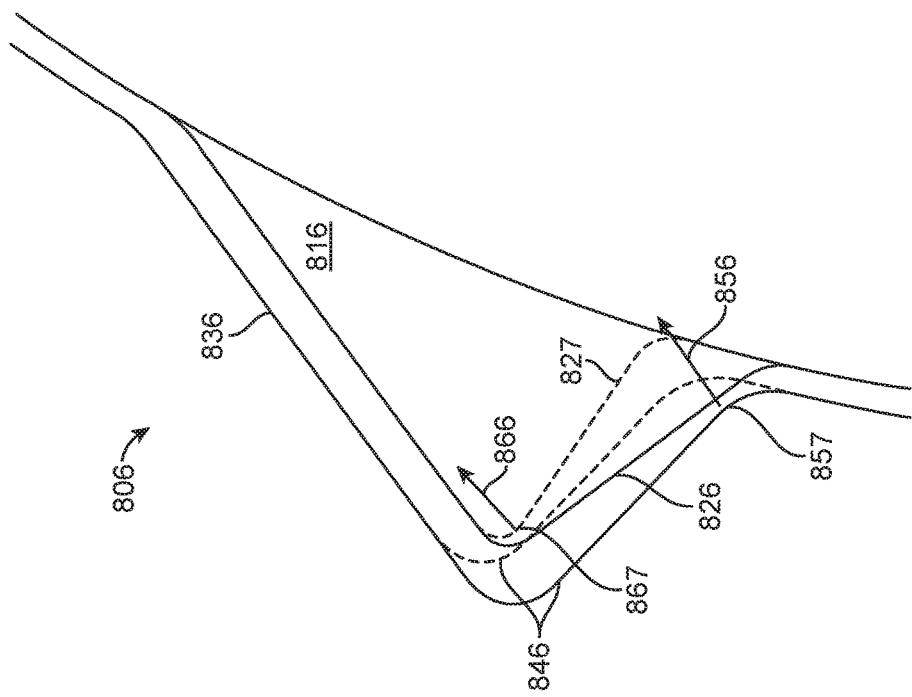
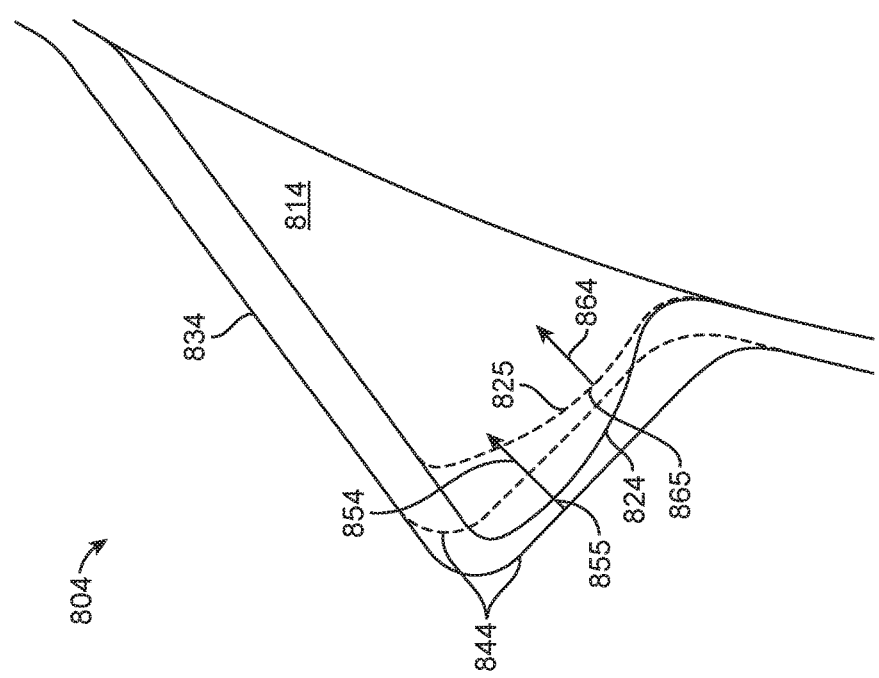
FIG. 8C
FIG. 8D

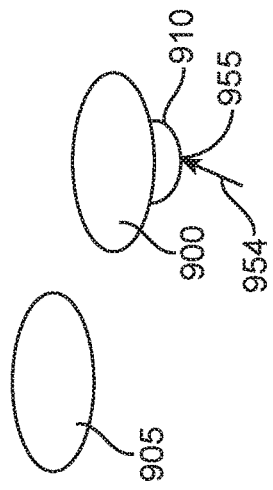
FIG. 9C
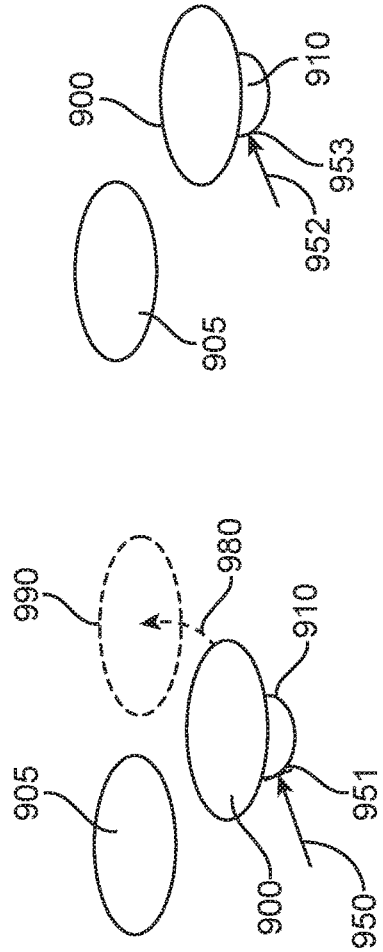
FIG. 9B
FIG. 9A
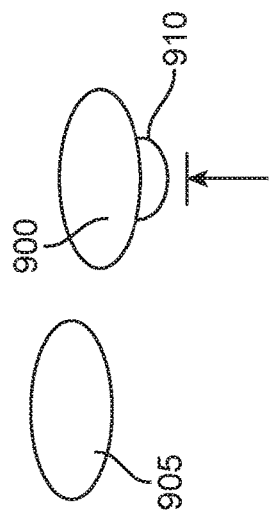
FIG. 9E
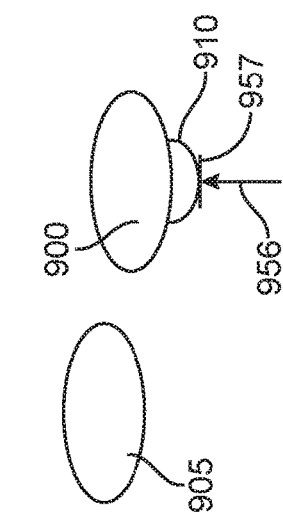
FIG. 9D

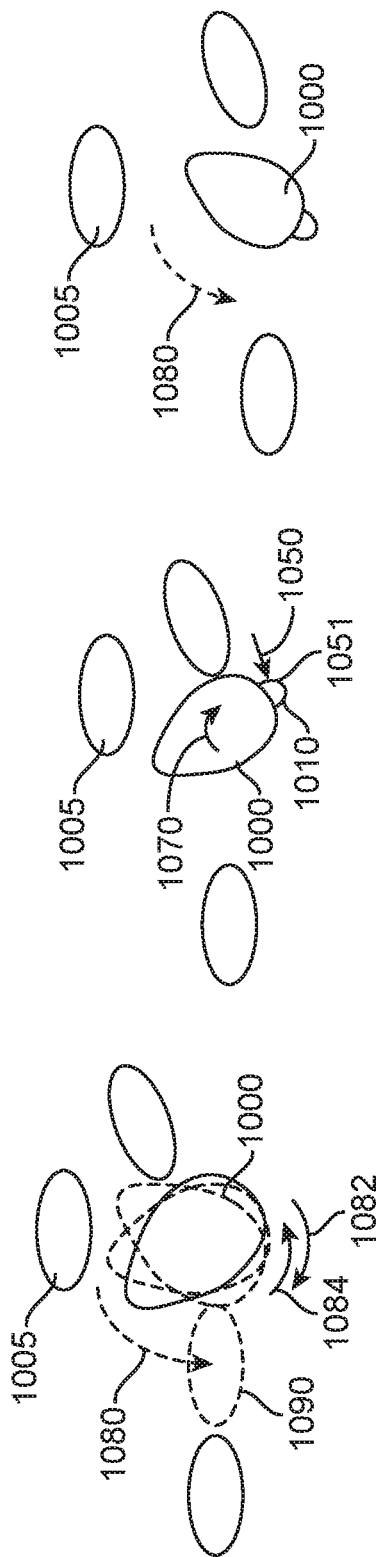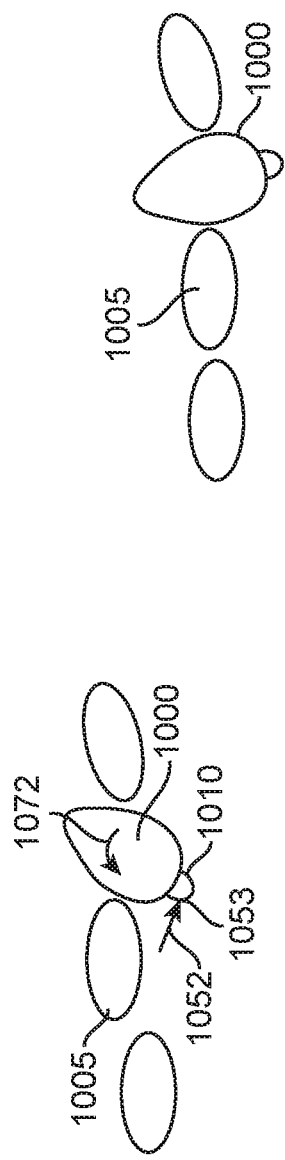

VARIABLE DIRECTION TOOTH ATTACHMENTS

BACKGROUND

Prior methods and apparatus for moving teeth can be less than ideal in at least some respects. Although orthodontic shell appliances can be effective in moving teeth, complex tooth movements may be benefit from the use of attachments on the teeth that engage the appliance to move the tooth. Although attachments can be effective, complex tooth movements may require multiple attachments on the teeth, which can be somewhat cumbersome and unsightly for the patient, as well as difficult for the orthodontic practitioner to apply. Furthermore, prior attachments can be sensitive to manufacturing variations resulting in unpredictable or inconsistent forces applied to teeth. It would be helpful to provide more versatile and reliable attachments, allowing the orthodontic shell appliances to move teeth more precisely and with less need to replace attachments during treatment.

SUMMARY

Embodiments of the present disclosure provide improved systems, methods, and apparatus for moving teeth. In many embodiments, the orthodontic systems herein include an attachment device having a convex surface. The convex surface can engage with an appliance shell to apply repositioning forces to teeth with improved reliability and reduced sensitivity to variations in manufacturing tolerances. The convex surface of the attachment further allows the application of a plurality of tooth moving forces by contacting the attachment surface at different locations with engagement surfaces of one or more appliances, sequentially and/or concurrently. In many embodiments, the direction of the tooth moving forces applied may be independently and continuously varied by continuously varying the contact location of an engagement portion of an appliance with the convex surface of the attachment. The tooth moving forces applicable by attachments as disclosed herein can be used to move teeth along any of a wide array of trajectories.

In one aspect, an orthodontic system for repositioning a patient's teeth is provided. The system comprises an attachment device configured to be coupled to a tooth of the patient and comprising a convex surface. The system also comprises a plurality of appliance shells each shaped to receive the patient's teeth, each appliance comprising an engagement portion positioned to engage the convex surface of the attachment device so as to apply a repositioning force to the tooth. The engagement portions of at least some of the plurality of appliance shells may each be arranged to contact the convex surface at a different respective location so as to apply different respective repositioning forces to the tooth.

In another aspect, a computer-implemented method for processing tooth movement data in order to design an orthodontic system for repositioning a patient's teeth is provided. The computer system receives tooth movement data indicative of a movement trajectory for a tooth of the patient, and processes data including the tooth movement data so as to determine a geometry for an attachment device to be coupled to the tooth, the attachment device comprising a convex surface. The computer system further processes data including the tooth movement data so as to determine geometries for a plurality of appliance shells, each shaped to receive the patient's teeth. The plurality of appliance shells for which the geometries are determined each comprise an engagement portion positioned to engage the convex surface of the attachment device so as to apply a repositioning force to the tooth. Optionally, the engagement portions of at least some of the plurality of appliance shells are each arranged to contact the convex surface at a different respective location so as to apply different respective repositioning forces to the tooth in order to move the tooth along the movement trajectory.

In another aspect, an orthodontic appliance for repositioning a patient's teeth is provided. The appliance comprises an attachment device configured to be coupled to a tooth of the patient and comprising a convex surface, as well as a shell comprising a plurality of cavities shaped to receive the patient's teeth. At least one cavity of the plurality of cavities comprises a receptacle shaped to receive the attachment device, and the receptacle comprises a planar surface positioned to engage the convex surface of the attachment device so as to apply a repositioning force to the tooth.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 5A illustrates an attachment with a convex surface and an appliance configured to engage that surface, in accordance with many embodiments;

FIG. 5B illustrates a plurality of appliances, each configured with a surface at a different angle so as to contact a single attachment at different locations, thereby applying different forces, in accordance with many embodiments;

FIGS. 8A-8D illustrate the reduced sensitivity of attachments engaged on convex surfaces to manufacturing variations, compared to attachments engaged on planar surfaces, in accordance with many embodiments;

FIGS. 9A-9E illustrate how a tooth may be moved in a complex trajectory while applying forces to a single attachment comprising one or more convex engagement surfaces, in accordance with many embodiments;

FIGS. 10A-10E illustrate the use of an attachment comprising one or more convex engagement surfaces to rotate a tooth in multiple directions to provide space to move a second tooth, thereby allowing a complex reorganization of teeth, in accordance with many embodiments;

DETAILED DESCRIPTION

Figure 1A:
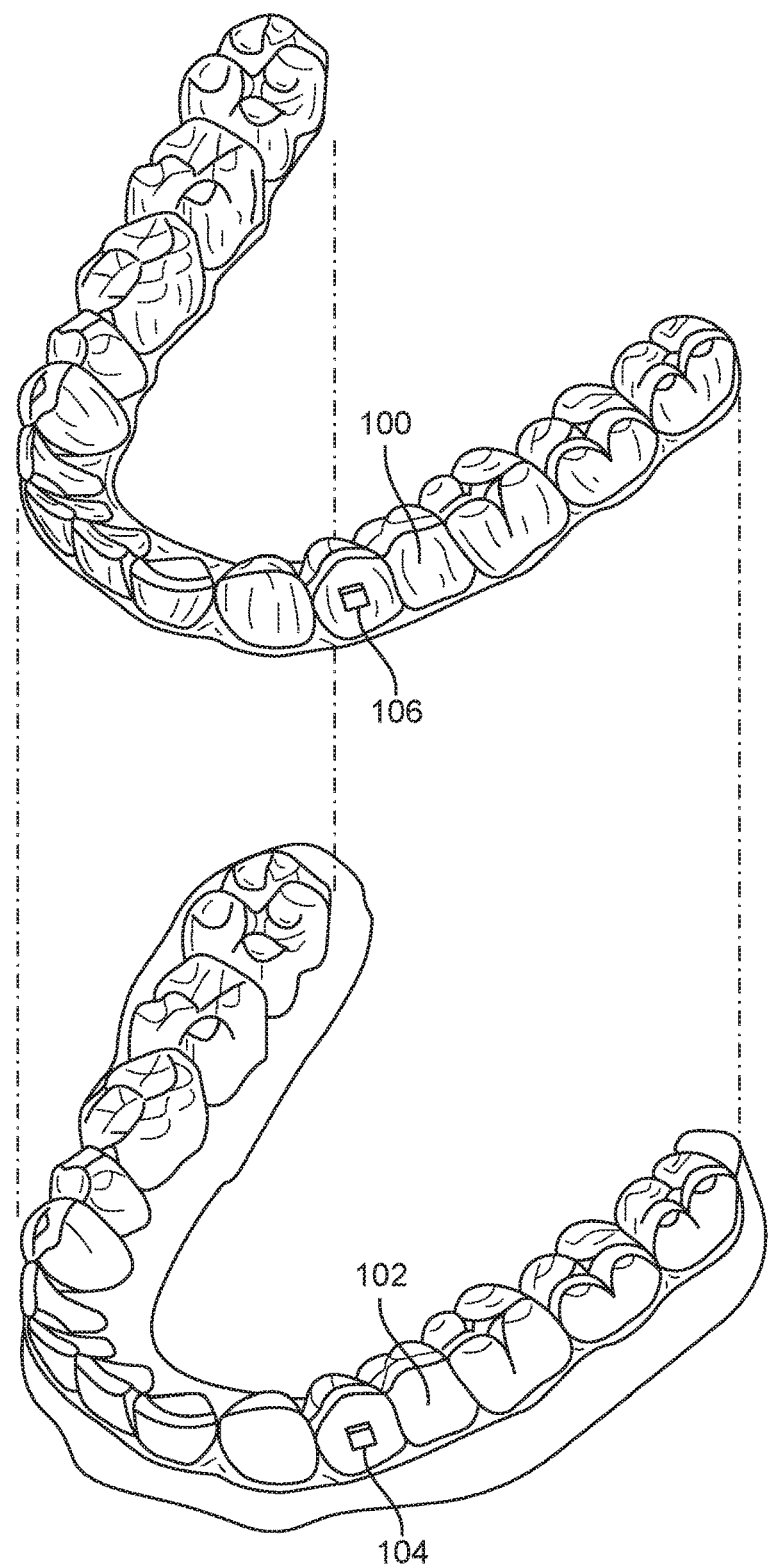
FIG. 1A illustrates a tooth repositioning appliance, in accordance with many embodiments.

The present disclosure provides improved systems, methods, and apparatus for moving a patient's teeth. In many embodiments, the orthodontic systems herein include an attachment device having a convex surface. The attachment device is attached to a tooth of a patient. The convex surface can engage with an appliance shell to apply repositioning forces to teeth with improved reliability and reduced sensitivity to variations in manufacturing tolerances. Additionally, the convex surface of the attachment further allows the application of a plurality of tooth moving forces by contacting the attachment surface at different locations with engagement surfaces of one or more appliances, sequentially and/or concurrently. In many embodiments, the direction of the tooth moving forces applied may be independently and continuously varied by continuously varying the contact location of an engagement portion of an appliance with the convex surface of the attachment. This can be advantageous, since it is often less expensive and difficult to replace or adjust a removable orthodontic appliance than to replace or adjust an attachment. Applying tooth moving forces using attachments as disclosed herein permits the movement of teeth along various trajectories, including complex trajectories, with greater reliability while allowing changes in direction without needing to replace the attachment.

As used herein the term "and/or" is used as a functional word to indicate that two words or expressions are to be taken together or individually. For example, A and/or B encompasses A alone, B alone, and A and B together.

In one aspect, an orthodontic system for repositioning a patient's teeth is provided. The system comprises an attachment device configured to be coupled to a tooth of the patient and comprising a convex surface. The system also comprises a plurality of appliance shells each shaped to receive the patient's teeth, each appliance shell comprising an engagement portion positioned to engage the convex surface of the attachment device so as to apply a repositioning force to the tooth. In many embodiments, the engagement portions of at least some of the plurality of appliance shells are each arranged to contact the convex surface at a different respective location so as to apply different respective repositioning forces to the tooth. Optionally, the engagement portions of some or all of the plurality of appliance shells may be arranged to contact the convex surface at the same location, e.g., to reduce susceptibility of appliance performance to manufacturing tolerances.

In many embodiments, the attachment device comprises a single convex surface.

In many embodiments, the convex surface comprises a spherical, ellipsoidal, or cylindrical shape profile.

In many embodiments, each engagement portion of each appliance shell comprises a planar surface, and the repositioning force applied by each engagement portion is oriented along a direction substantially normal to the planar surface. The amount of friction between the planar surface of the engagement portion and the convex surface of the attachment device may be relatively low resulting in minimal or no tangential forces. In some embodiments, the planar surfaces of the at least some of the plurality of appliance shells are each arranged at different orientations relative to the convex surface.

In many embodiments, the different respective repositioning forces differ from each other with respect to one or more of location or orientation.

In many embodiments, the different respective repositioning forces are configured to reposition the tooth along a non-linear movement trajectory.

In many embodiments, each engagement portion is positioned so as to contact the convex surface of the attachment device at a single location.

In many embodiments, at least one of the plurality of appliance shells comprises a plurality of engagement portions positioned to contact the convex surface at a plurality of different locations.

In many embodiments, the attachment device further comprises a non-contacting surface that does not engage the plurality of appliance shells. The non-contacting surface may be a convex surface or a non-convex surface.

In many embodiments, the system further comprises a second plurality of appliance shells each shaped to receive the patient's teeth, each appliance shell of the second plurality of appliance shells comprising an engagement portion positioned to engage the convex surface of the attachment device so as to apply a repositioning force to the tooth, wherein the engagement portions of at least some of the second plurality of appliance shells are each arranged to contact the convex surface at the same location so as to apply similar repositioning forces to the tooth.

In another aspect, a computer-implemented method for processing tooth movement data in order to design an orthodontic system for repositioning a patient's teeth is provided. The computer system receives tooth movement data indicative of a movement trajectory for a tooth of the patient, and processes data including the tooth movement data so as to determine a geometry for an attachment device to be coupled to the tooth, the attachment device comprising a convex surface. The computer system further processes data including the tooth movement data so as to determine geometries for a plurality of appliance shells, each shaped to receive the patient's teeth. The plurality of appliance shells for which the geometries are determined each comprise an engagement portion positioned to engage the convex surface of the attachment device so as to apply a repositioning force to the tooth. Optionally, the engagement portions of at least some of the plurality of appliance shells may each be arranged to contact the convex surface at a different respective location so as to apply different respective repositioning forces to the tooth in order to move the tooth along the movement trajectory.

In many embodiments, the attachment device comprises a single convex surface.

In many embodiments, the convex surface comprises a spherical, ellipsoidal, or cylindrical surface profile.

In many embodiments, each engagement portion of each appliance shell comprises a planar surface, and the repositioning force applied by each engagement portion is oriented along a direction substantially normal to the planar surface. In some embodiments, the planar surfaces of the at least some of the plurality of appliance shells are each arranged at a different orientation relative to the convex surface.

In many embodiments, the different respective repositioning forces differ from each other with respect to one or more of location or orientation.

In many embodiments, the method further comprises calculating one or more forces or moments to move the tooth along the movement trajectory. The different repositioning forces applied correspond to at least a subset of the one or more forces or moments.

In many embodiments, the movement trajectory comprises a non-linear movement trajectory.

In many embodiments, the movement trajectory is configured to produce round-tripping of the tooth. As used herein, "round-tripping" may refer to a sequence of movements in which a tooth moves away from an initial position and/or orientation (e.g., to avoid colliding with another tooth) and then moves at least partially back towards the initial position and/or orientation.

In many embodiments, each engagement portion is positioned so as to contact the convex surface of the attachment device at a single location.

In many embodiments, at least one of the plurality of appliance shells comprises a plurality of engagement portions positioned to contact the convex surface at a plurality of different locations.

In many embodiments, the attachment device further comprises a non-contacting surface that does not engage the plurality of appliance shells. The non-contacting surface may be a convex surface or a non-convex surface.

In many embodiments, the method further comprises outputting digital data indicative of the determined geometries of the plurality of appliance shells.

In another aspect, an orthodontic appliance for repositioning a patient's teeth is provided. The appliance comprises an attachment device configured to be coupled to a tooth of the patient and comprising a convex surface, as well as a shell comprising a plurality of cavities shaped to receive the patient's teeth. At least one cavity of the plurality of cavities comprises a receptacle shaped to receive the attachment device, and the receptacle comprises a planar surface positioned to engage the convex surface of the attachment device so as to apply a repositioning force to the tooth.

Optionally, the planar surface is positioned to engage the convex surface at a single location to apply the repositioning force to the tooth.

In many embodiments, the convex surface comprises a spherical, ellipsoidal, or cylindrical shape profile.

In many embodiments, the repositioning force applied by the planar surface is oriented along a direction substantially normal to the planar surface.

In many embodiments, the attachment device further comprises a non-contacting surface that does not engage the planar surface. The non-contacting surface may be a convex surface or a non-convex surface.

In another aspect, an orthodontic system for repositioning a patient's teeth is provided. The system comprises an attachment device configured to be coupled to a tooth of the patient and comprising a convex surface. The system also comprises a plurality of appliance shells each shaped to receive the patient's teeth, each appliance shell comprising an engagement portion positioned to engage the convex surface of the attachment device so as to apply a repositioning force to the tooth. In many embodiments, the engagement portions of at least some of the plurality of appliance shells are each arranged to contact the convex surface at the same location so as to apply repositioning forces to the tooth.

In many embodiments, the attachment device comprises a single convex surface.

In many embodiments, the convex surface comprises a spherical, ellipsoidal, or cylindrical shape profile.

In many embodiments, each engagement portion of each appliance shell comprises a planar surface, and the repositioning force applied by each engagement portion is oriented along a direction substantially normal to the planar surface. The amount of friction between the planar surface of the engagement portion and the convex surface of the attachment device may be relatively low resulting in minimal or no tangential forces. In some embodiments, the planar surfaces of the at least some of the plurality of appliance shells are arranged at the same orientation relative to the convex surface.

In many embodiments, each engagement portion is positioned so as to contact the convex surface of the attachment device at a single location.

In many embodiments, the attachment device further comprises a non-contacting surface that does not engage the plurality of appliance shells. The non-contacting surface may be a convex surface or a non-convex surface.

In many embodiments, the system further comprises a second plurality of appliance shells each shaped to receive the patient's teeth, each appliance shell of the second plurality of appliance shells comprising an engagement portion positioned to engage the convex surface of the attachment device so as to apply a repositioning force to the tooth, wherein the engagement portions of at least some of the second plurality of appliance shells are each arranged to contact the convex surface at a different location so as to apply different repositioning forces to the tooth.

In another aspect, a computer-implemented method for processing tooth movement data in order to design an orthodontic system for repositioning a patient's teeth is provided. The computer system receives tooth movement data indicative of a movement trajectory for a tooth of the patient, and processes data including the tooth movement data so as to determine a geometry for an attachment device to be coupled to the tooth, the attachment device comprising a convex surface. The computer system further processes data including the tooth movement data so as to determine geometries for a plurality of appliance shells, each shaped to receive the patient's teeth. The plurality of appliance shells for which the geometries are determined each comprise an engagement portion positioned to engage the convex surface of the attachment device so as to apply a repositioning force to the tooth. Optionally, the engagement portions of at least some of the plurality of appliance shells may each be arranged to contact the convex surface at the same location so as to apply repositioning forces to the tooth in order to move the tooth along the movement trajectory.

In many embodiments, the attachment device comprises a single convex surface.

In many embodiments, the convex surface comprises a spherical, ellipsoidal, or cylindrical surface profile.

In many embodiments, each engagement portion of each appliance shell comprises a planar surface, and the repositioning force applied by each engagement portion is oriented along a direction substantially normal to the planar surface. In some embodiments, the planar surfaces of the at least some of the plurality of appliance shells are each arranged at the same orientation relative to the convex surface.

In many embodiments, the method further comprises calculating one or more forces or moments to move the tooth along the movement trajectory. The repositioning forces applied correspond to at least a subset of the one or more forces or moments.

In many embodiments, each engagement portion is positioned so as to contact the convex surface of the attachment device at a single location.

In many embodiments, the attachment device further comprises a non-contacting surface that does not engage the plurality of appliance shells. The non-contacting surface may be a convex surface or a non-convex surface.

In many embodiments, the method further comprises outputting digital data indicative of the determined geometries of the plurality of appliance shells.

The embodiments disclosed herein are well suited for combination with one or known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

Orthodontic systems of the present disclosure can include tooth attachments and one or more orthodontic appliances that engage the attachments when worn by a patient. Appliances having teeth receiving cavities that receive and reposition teeth, e.g., via application of force due to appliance resiliency, are generally illustrated with regard to FIG. 1A. FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
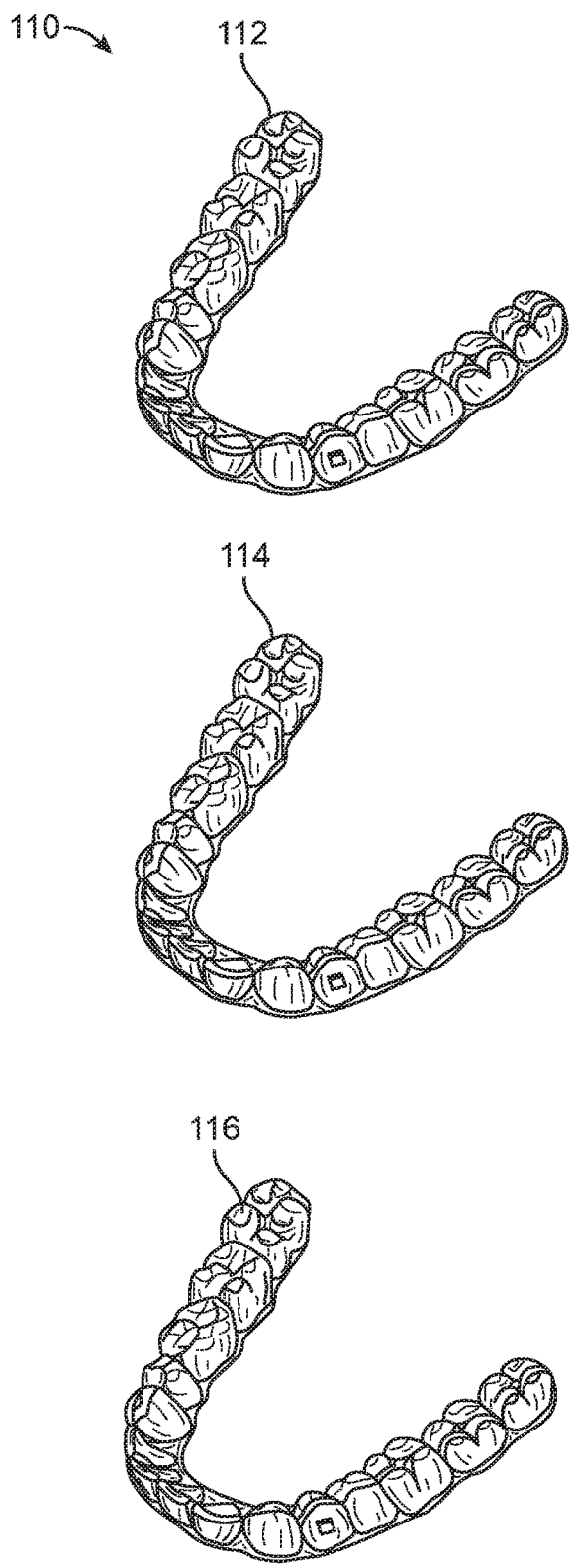
FIG. 1B illustrates a tooth repositioning system, in accordance with many embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In many embodiments, orthodontic appliances, such as the appliance illustrated in FIG. 1A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof. Tooth movement of the crown greater than the movement of the root can be referred to as tipping. Equivalent movement of the crown and root can be referred to as translation. Movement of the root greater than the crown can be referred to as root movement.

Figure 2:
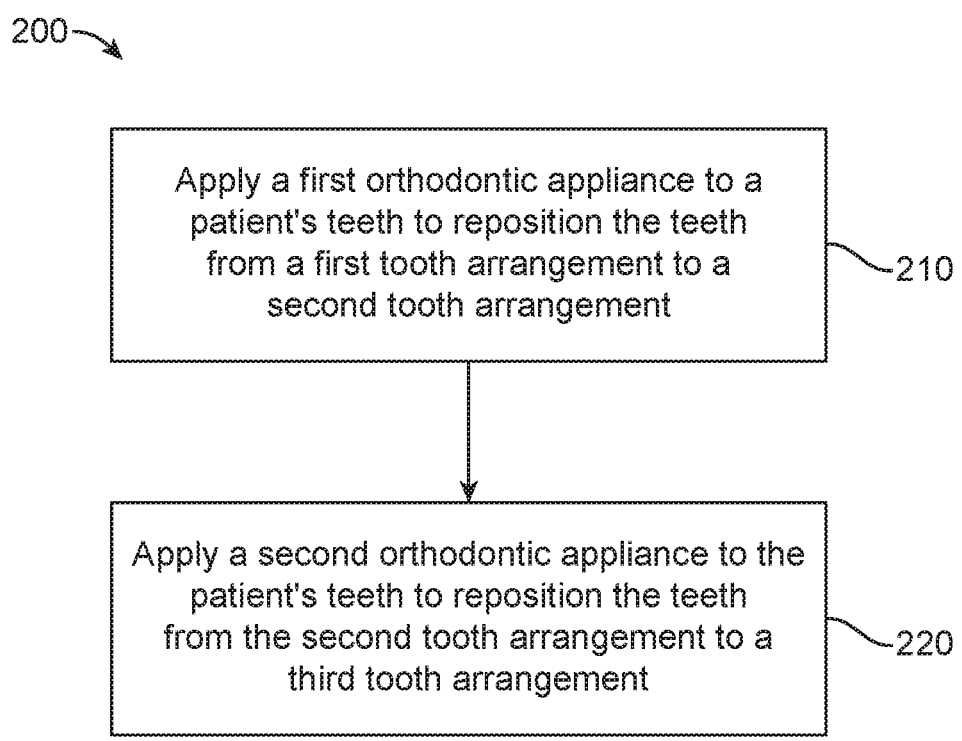
FIG. 2 illustrates a method of orthodontic treatment using a plurality of appliances, in accordance with many embodiments.

FIG. 2 illustrates a method 200 of orthodontic treatment using a plurality of appliances, in accordance with many embodiments. The method 200 can be practiced using any of the appliances or appliance sets described herein. In step 210, a first orthodontic appliance is applied to a patient's teeth in order to reposition the teeth from a first tooth arrangement to a second tooth arrangement. In step 220, a second orthodontic appliance is applied to the patient's teeth in order to reposition the teeth from the second tooth arrangement to a third tooth arrangement. The method 200 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The orthodontic systems described herein can include one or more tooth-mounted attachment devices (also referred to herein as "attachments") that engage a portion of an orthodontic appliance, such as a shell appliance, in order to apply a force to the underlying tooth. An attachment device can be fabricated using various methods. For example, a pre-formed attachment device (e.g., directly fabricated by rapid prototyping, 3D-printing, etc.) having a specified geometry can be bonded to the patient's tooth at a target location on the tooth surface using light-curable adhesives and the like. Alternatively, the attachment can be formed in situ on the patient's tooth using a template having a recess defining the attachment geometry, the recess being filled with a curable material. In many embodiments, the template is a shell appliance that, when worn on the patient's teeth, positions the recess filled with material over the target location on the tooth surface. The material can then be cured, e.g., with light energy, in order to form and bond the attachment to the tooth surface.

Use of attachment devices may be advantageous for exerting repositioning forces that would otherwise be difficult to achieve using a shell appliance alone. In many embodiments, an attachment device includes one or more surfaces arranged to engage (e.g., contact) a corresponding portion of an appliance shell when the shell is worn on patient's teeth, and the engagement between the attachment surface(s) and shell portion can produce forces that elicit tooth movement. The geometry (e.g., size, shape) and/or location (e.g., position, orientation) of the attachment device can be varied as desired to produce the desired tooth movement force(s). For example, the attachment devices herein can be any suitable shape, such as a portion of a sphere, ellipse, ovoid, cylinder, or a curved and/or flat polyhedral shape. In many embodiments, the portion of the appliance that touches the tooth may be shaped to substantially match the shape of the tooth surface. Similarly, as described above and herein, the surface(s) of an attachment device that engage the appliance can have any suitable shape, such as a spherical, ellipsoidal, or cylindrical shape profile, or even further profiles that comprise a substantially convex curve along at least one dimension. In some embodiments, at least one surface of an attachment device that engages the appliance may be substantially planar.

In many embodiments, the appliance shell is shaped to accommodate the attachment device when the shell is placed on the patient's teeth. For example, the appliance shell can include an engagement portion positioned to engage (e.g., contact) one or more surfaces of the attachment device. Optionally, the engagement portion can be part of a receptacle or recess in the appliance shell that receives the attachment or a portion thereof. The engagement portion can have any suitable shape, such as substantially planar, convex, or even concave surfaces. The engagement portion can have a shape complementary to that of the attachment surface(s) in order to provide mating contact with the surface(s) when the appliance is worn, e.g., a planar engagement portion is used in combination with a planar attachment surface. The engagement portion can alternately have a shape that differs substantially from the shape of the attachment surface, such as an engagement portion comprising a substantially planar surface in combination with a convex attachment surface, or a convex appliance surface in combination with a substantially planar attachment surface. In many embodiments, the engagement portion of the appliance includes a surface having a curvature that differs from the curvature of the corresponding attachment surface(s).

The various surfaces of attachments and appliances are described herein variously using terms such as "planar," "convex," or "concave." It will be further understood that when using each of these terms, included in the idea are surfaces substantially similar to such surfaces. Thus, planar surfaces as described herein include substantially planar surfaces, convex surfaces include substantially convex surfaces, and concave surfaces include substantially concave surfaces. In some embodiments, surface irregularities or roughness, such as those due to manufacturing limitations, may be ignored in defining convex, concave, or planar surfaces if they are small compared to the size of the surface as a whole (e.g., at least one or two orders of magnitude smaller). Thus, for example, an approximately ellipsoidal surface portion with a surface area of 4 square mm and a depth of 1 mm from edge to outermost point would be considered to be a substantially convex surface, even if it had surface irregularities, for example, on the 0.1 mm scale.

The curvature of a convex surface, such as a convex surface of an attachment, may be chosen in a variety of ways. For example, the convex surface may be shaped like a portion of a sphere or an ellipsoid, or may be a shape substantially similar to such a surface, such as ovoid shapes, for example. Other surfaces may be also chosen, such as portions of cylindrical surfaces, which may be used to allow variable force directions around the radius of the cylinder without allowing substantial variation along the axis of the cylinder.

The curvature of an attachment surface or appliance surface can be characterized in a variety of ways. For example, the degree of concavity or convexity may be determined based on the radius of curvature of the surface. In some embodiments, a concave or convex surface of an attachment or appliance has a radius of curvature less than or equal to about 10 mm, less than or equal to about 50 mm, less than or equal to about 100 mm, less than or equal to about 150 mm, or less than or equal to about 200 mm. In some embodiments, the radius of curvature is within a range from about 0.5 mm to about 10 mm, within a range from about 1 mm to about 10 mm, within a range from about 3 mm to about 10 mm, within a range from about 10 mm to about 50 mm, within a range from about 10 mm to about 100 mm, within a range from about 10 mm to about 200 mm, within a range from about 50 mm to about 100 mm, within a range from about 50 mm to about 150 mm, within a range from about 50 mm to about 200 mm, within a range from about 100 mm to about 150 mm, or within a range from about 150 mm to about 200 mm. In some embodiments, a planar surface of an attachment or appliance has as radius of curvature of greater than or equal to about 10 mm.

In some embodiments, the degree of concavity or convexity of an attachment surface may be determined based on the ratio of the radius of curvature of the surface to the half-size of the attachment. The term "half-size" may be used herein to refer to the radius of the circle having a surface area equivalent to the lateral surface area (e.g., surface area attached to the tooth surface) of the attachment. In some embodiments, a convex or concave attachment surface has a radius of curvature that is approximately the same order of magnitude as the half-size of the attachment. In some embodiments, the ratio of radius of curvature to half-size for a convex or concave attachment surface is less than or equal to about 50. In some embodiments, the ratio of radius of curvature to half-size for a planar attachment surface is greater than or equal to about 50.

As another example, the ratio of the depth to a size of a surface may be used to characterize it as substantially planar, convex, or concave. The size of a surface may be determined by taking the square root of its area. The depth of a surface may be determined as follows: given a plane that minimizes the mean square distance from the plane to the perimeter of the surface, the depth is the sum of the distances in each direction from that plane to the farthest point on the surface. In some embodiments, the attachments herein include convex surfaces wherein the size-to-depth ratio is within a range from about 1:100 to about 1:10, or within a range from about 1:10 to about 1:2. In further embodiments, an attachment can have a convex surface with a size-to-depth ratio of about 1, or within a range from about ½ to about 2, or even larger ratios, such as within a range from about 2 to about 10, within a range from about 10 to about 100, or even greater.

Figure 3:
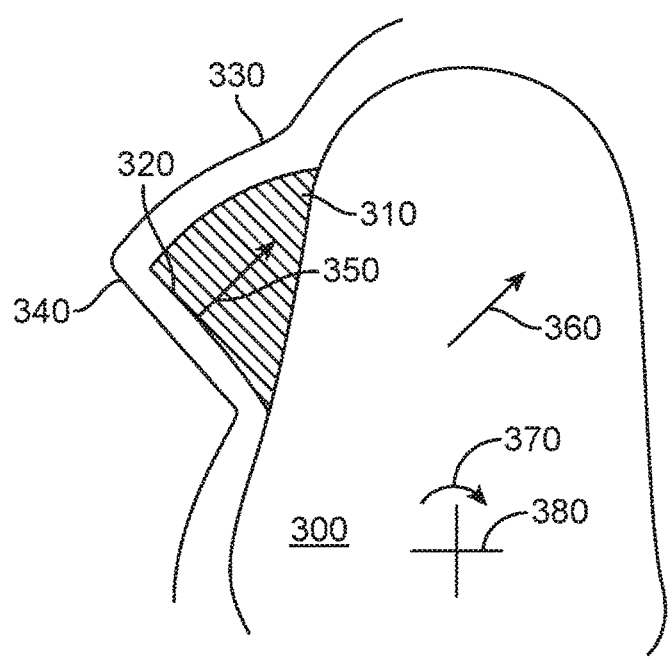
FIG. 3 illustrates the interface between an attachment comprising a planar surface and an engagement portion of an appliance comprising a planar surface, in accordance with many embodiments.

FIG. 3 illustrates the interface between an attachment comprising a planar surface and an engagement portion of an appliance comprising a planar surface. An attachment 310 comprising a planar surface 320 is bonded to a tooth 300. Part of an orthodontic shell appliance 330 is shown as worn in the mouth of a patient, the appliance having an engagement portion comprising a planar surface 340. Optionally, the appliance 330 can include a recess or receptacle shaped to receive the attachment 310 or a portion thereof, and the planar surface 340 of the engagement portion can form part of the recess or receptacle. The orthodontic appliance 330 is designed such that when worn, the planar surface 340 of the engagement portion engages the planar surface 320 of the attachment 310. This engagement produces a force 350 on the attachment 310. Because the attachment 310 is bonded to the tooth 300, the force 350 causes a tooth moving force 360, and may also apply a moment 370 on the tooth 300.

The magnitude and direction of the tooth moving force 360 may be determined by the shape and/or material properties of the orthodontic appliance 330 and of the attachment 310. The magnitude of the tooth moving force 360 may depend on the elasticity of the appliance 330, the attachment (e.g., the attachment 310 is typically a relatively rigid material compared to the appliance), and the degree to which the planar appliance surface 340 is deflected from its unloaded or rest state when it comes into contact with the planar attachment surface 320. The direction of the tooth moving force may be determined by the angle at which the attachment surface 320 and appliance surface 340 come into contact. In some embodiments, friction may be relatively low for appliance and attachment surfaces contacting within a patient's mouth, so the force 350, as well as corresponding tooth moving force 360, will point in a direction substantially normal to the engaged appliance and attachment surfaces, which may be designed to be parallel or substantially parallel to each other.

The moment 370 may be determined by the magnitude and direction of the tooth moving force 360 as well as the displacement vector from the center of rotation 380 of the tooth to the location of engagement between surfaces 320 and 340, e.g., as a vector cross-product of the tooth moving force 360 and the displacement vector. In embodiments where planar surfaces such as appliance surface 340 and attachment surface 320 are designed to be parallel, the contact location of the surfaces may be approximated as the center of the two surfaces. However, if the two surfaces contact each other at an unintended location, for example due to imperfect fabrication of the appliance and/or attachment, undesired forces and moments can be produced. For example, if an appliance and an attachment are fabricated with planar surfaces that are not substantially parallel, they may only contact at the edge of the surfaces, rather than continuously across the center of the surfaces as intended. This can result in forces and/or moments that differ dramatically from the expected values, which may in turn lead to an unwanted tooth movement.

Figure 4B:
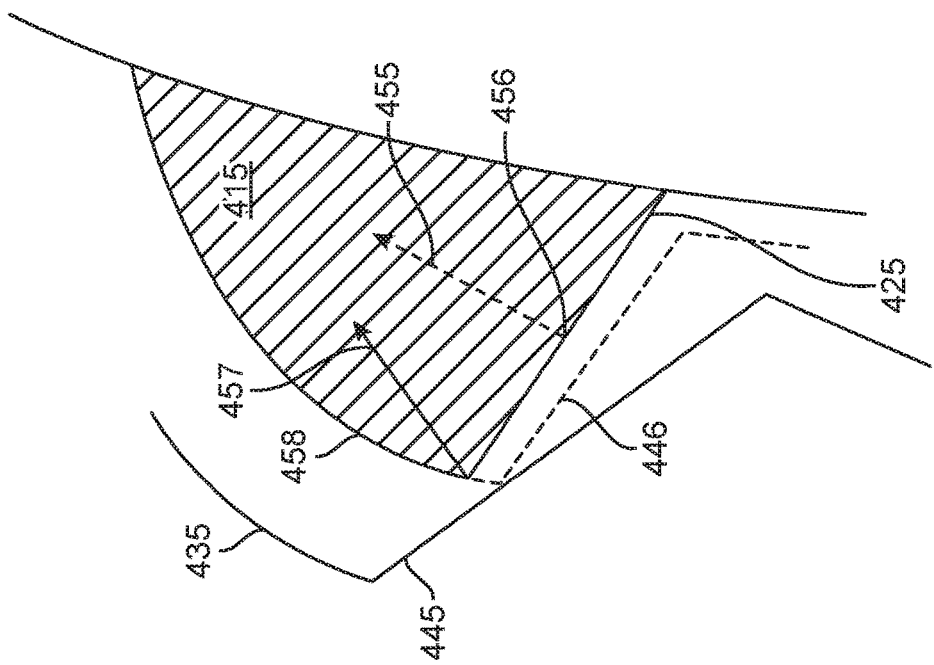
FIGS. 4A and 4B illustrate how small errors in appliance fabrication can lead to large changes in the location of interaction between a planar appliance surface and a planar attachment surface, in accordance with many embodiments.
Figure 4A:
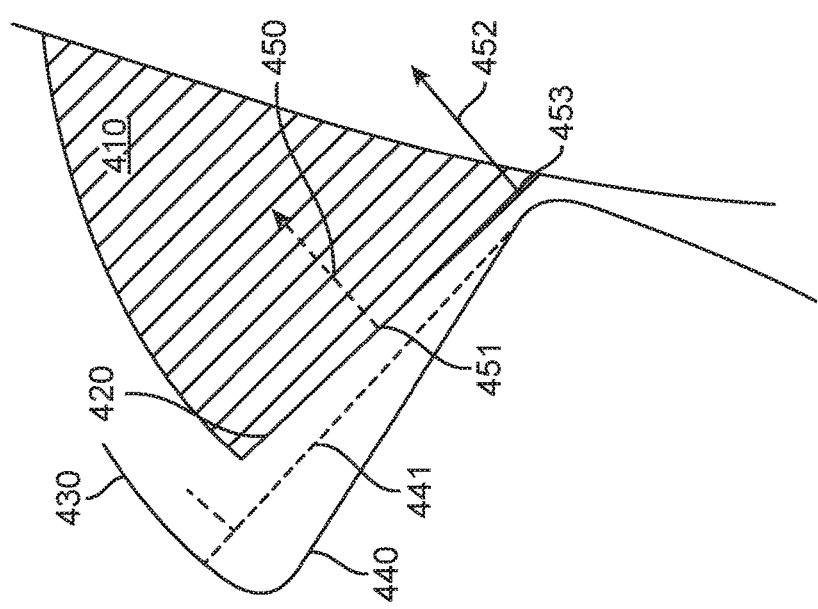

FIGS. 4A and 4B illustrate how small errors in appliance fabrication can lead to large changes in the location of interaction between a planar appliance surface and a planar attachment surface.

FIG. 4A illustrates an appliance 430 with an engagement portion comprising an appliance surface 440 configured to engage an attachment surface 420 of a dental attachment 410. In the depicted embodiment, the intended appliance surface 441 is oriented parallel to the attachment surface 420, in order to produce a desired force 450 at or near the center 451 of the attachment surface. However, if the actual appliance surface 440 is oriented at an angle rotated counterclockwise from the intended surface 441, e.g., due to imperfect manufacturing, the appliance instead produces a force 452 located near the end of the attachment surface 420, at contact location 453. Because the engagement surfaces are substantially planar, even a very small change in angle of the appliance surface 440 can cause a large difference in contact location. This can result in a moment vector being applied to the tooth that is significantly different from the desired value.

FIG. 4B shows a similar problem that can occur when the angle of an appliance surface has an error in the opposite direction. An appliance 435 with an engagement portion comprising an appliance surface 445 is configured to engage an attachment surface 425 of a dental attachment 415. The intended appliance surface 446 is parallel to the attachment surface 425, in order to produce a desired force 455. This is illustrated by intended surface 446. However, if the actual appliance surface 445 is oriented at an angle rotated clockwise from the intended surface 446, e.g., due to imperfect manufacturing, the appliance instead produces a force 457 located near the end of the attachment surface 425, at contact location 458. Because the attachment and appliance surfaces are planar, even a very small change in angle of the appliance surface 440 can cause a large difference in contact location. This can result in a moment vector being applied to the tooth that is significantly different from the desired value. Furthermore, because the contact location 458 is at an edge of the attachment surface 425, the magnitude and direction of the resulting force 457 may differ significantly from the desired force 455. Furthermore, the sharp attachment corner at contact location 458 can cause the magnitude of resulting force 457 to depend strongly on the shape of the attachment corner, such that small manufacturing imperfections can lead to large changes in force magnitude and/or direction.

As illustrated by FIGS. 4A and 4B, the use of attachments with planar surfaces to engage appliances with planar surfaces can lead to difficulties in creating desired forces and moments, with small manufacturing defects or variations leading to large changes in force and/or moment. Such manufacturing defects or variations may arise due to inaccuracies in fabricating the appliance (e.g., by direct fabrication or indirect fabrication via thermoforming over a mold), as well as inaccuracies in fabricating the attachment device, and can result in an appliance and/or attachment geometry that differs from the intended geometry (e.g., with respect to shape, position, and/or orientation). Furthermore, even absent manufacturing defects, providing proper engagement between attachment and appliance means that planar attachment surfaces may be limited in the range of planar appliance surfaces they can engage: for example, if the two planes are not substantially parallel, they may interact in unpredictable or undesirable ways. When friction is relatively low, a configuration of parallel planes can be limited in some instances to only producing a force in a single direction: substantially normal to the surface of the attachment.

In some embodiments, the attachment devices and appliances disclosed herein address these issues by replacing the engaged planar surface of an attachment with a convex surface, allowing different appliances to be manufactured to produce different forces, while also making the system as a whole more robust against manufacturing defects.

FIG. 5A illustrates an attachment with a convex surface and a portion of an appliance shell configured to engage that surface, in accordance with embodiments. An attachment 510 with a convex attachment surface 520 is bonded to a tooth 500. The attachment 510 can be used in conjunction with an appliance shell 530 with a receptacle to accommodate and receive the attachment 510. The appliance 530 includes an engagement portion comprising an appliance surface 540 that contacts the convex attachment surface 520 at contact location 551, generating a force 550 on the attachment 510, and thus a similar tooth moving force on the tooth 500 to which the attachment is bonded.

In many embodiments, the engagement portion of the appliance comprises an appliance surface 540 that is substantially planar, as depicted. However, in alternative embodiments, it may also be designed to be convex (bending away from the attachment), or even concave (bending toward the attachment). In embodiments where the engagement surface is concave, the magnitude of its curvature may be less than that of the convex attachment surface so as to permit contact with the convex attachment surface at a single location. The curvature of the appliance and the attachment away from the contact location may be varied as desired. For example, in some embodiments, appliance 530 also comprises a concave portion 560 with greater curvature than the convex attachment engagement surface 520, but because the concave portion 560 does not engage the convex attachment engagement surface 520, the force applied by the contact between the appliance and the attachment is not affected. One of ordinary skill in the art would appreciate that since the inner surface of the appliance contacts the outer surface of the attachment, a convex attachment engagement surface has the same absolute direction of curvature as a concave appliance engagement surface, and vice versa.

In the depicted embodiment, the appliance surface 540 is arranged to contact the convex attachment surface 520 at a single location 551 on the attachment 510 such that the force 550 is applied to the tooth 500 localized about that location. The position of contact location 551 is determined by the shape of the convex attachment surface 520 and the slope of the appliance surface 540: in the case of a planar appliance engagement surface, for example, the two may contact at the point where the appliance surface is substantially tangent to the attachment surface. The direction of force can likewise be determined by the two surfaces: when friction is low, the force 550 may be determined to be in a direction substantially normal to the two engagement surfaces at their contact location 551, with minimal or no force components are produced along the direction tangential to the attachment surface. "Substantially normal" may be used herein to refer to an angle within a range from about 89° to about 91°, from about 85° to about 95°, or from about 75° to about 105°. Thus, it can be appreciated that the direction of the applied tooth moving force can be determined—and varied—by varying the location and orientation of the appliance surface relative to the attachment device, thereby changing both the location and orientation of the resultant tooth moving force.

FIG. 5B illustrates a plurality of appliances, each configured with a surface at a different angle so as to contact a single attachment at different locations, thereby applying different forces, in accordance with embodiments. In each of configurations 502, 504, and 506, a different respective shell appliance 532, 534, and 536 engages the same attachment 510. Each appliance has a respective engagement portion comprising an appliance surface 542, 544, and 546, each surface being oriented at a different respective angle 543, 545, and 547. The different angles of the surfaces of appliances 532, 534, and 536 cause the engagement portion of each appliance to engage the convex surface of attachment 510 at a different respective location 553, 555, and 557, thereby producing different respective tooth moving forces 552, 554, and 556, in a direction substantially normal to the respective appliance surfaces 542, 544, and 546. Due to the different contact locations 553, 555, and 557, in conjunction with the different tooth moving forces 552, 554, and 556, it will likewise be appreciated that each appliance applies a different moment to the tooth as well. Thus, a single attachment comprising a convex surface may be used to produce a plurality of different forces and/or a plurality of different moments, by sequentially contacting a plurality of appliances to the attachment at different locations. It will be appreciated that in many embodiments, the force direction applied by each appliance shell may be independently chosen from a substantially continuous distribution by designing the appliance such that the engagement portion contacts the attachment surface at a location chosen from a corresponding, substantially continuous distribution of contact locations along the attachment surface. This permits the movement of a tooth along a complex, continuously variable trajectory using only a single attachment, as discussed further herein.

In many embodiments, an attachment device comprises only a single continuous convex surface. In alternative embodiments, an attachment device may comprise a plurality of different surfaces. These surfaces may comprise multiple convex surfaces, or even mixes of convex, concave, and/or planar surfaces. In some embodiments, an appliance may be configured to concurrently engage a plurality of attachment surfaces, such as a plurality of convex attachment surfaces or even a mixture of attachment surfaces. For example, an appliance might concurrently and/or sequentially engage both convex and planar surfaces of an attachment. In some embodiments, the attachment device includes one or more non-contacting surfaces that do not engage (e.g., contact) any portion of the appliance surface when the appliance is worn by the patient. The geometry of a non-contacting surface may be varied as desired, e.g., planar, convex, or non-convex.

Figure 6:
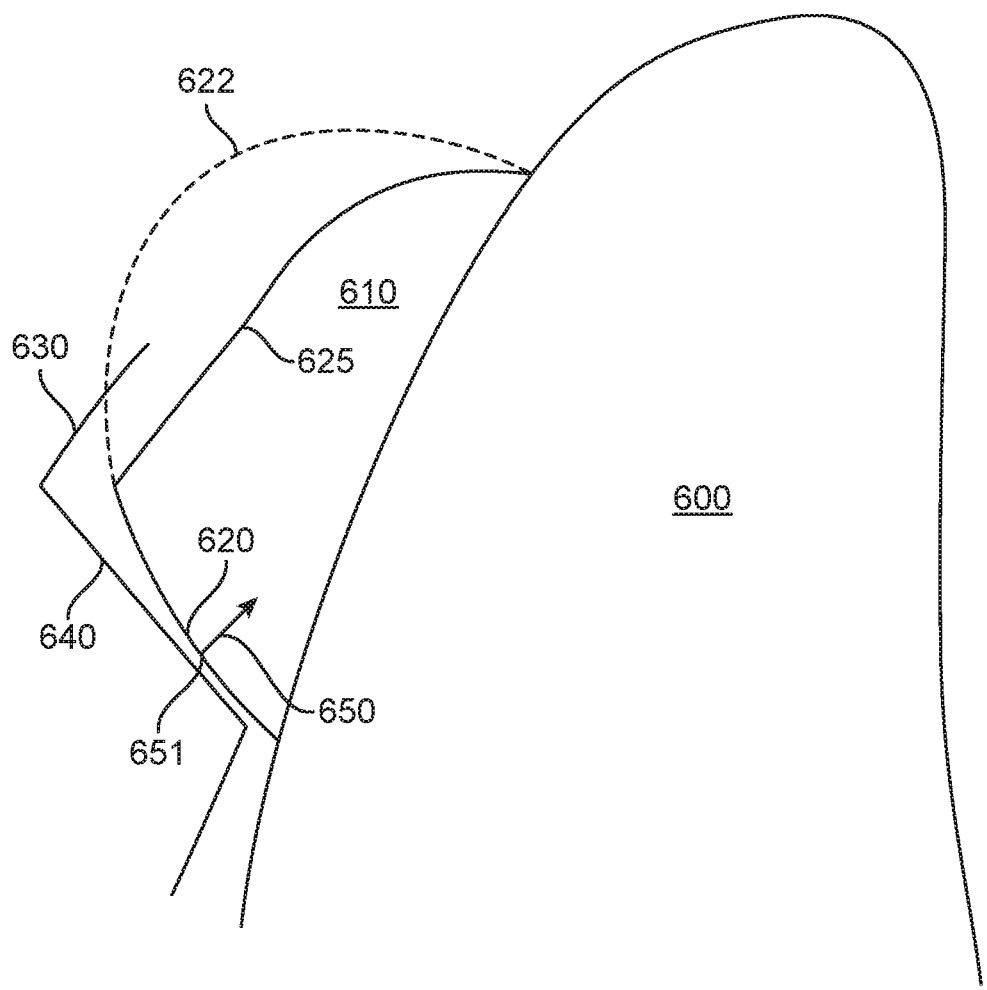
FIG. 6 illustrates an attachment comprising a convex surface and a non-contacting surface, in addition to an appliance with a surface configured to engage the convex surface, in accordance with many embodiments.

FIG. 6 illustrates a tooth 600 to which is bonded an attachment 610 comprising both a convex surface 620 and a non-contacting surface 625. FIG. 6 also illustrates an appliance 630 with an engagement portion comprising a surface 640 configured to engage the convex surface 620, in accordance with embodiments. As illustrated in the figure, the convex surface 620 protrudes outward, presenting a contact location 651 that is tangent to the appliance engagement surface 640, and at which the two will meet. The tooth moving force 650 applied by the appliance points in a direction substantially normal to both the appliance surface 640 and the convex attachment surface 620 at their point of contact 651. As can be readily appreciated, the direction of force may be varied smoothly by varying the angle of appliance surface 640, for example using a plurality of appliances, which will also correspondingly smoothly shift the point of contact 651.

The attachment 610 may also include a non-contacting surface 625 that does not engage (e.g., contact) the appliance 630, and therefore does not directly transmit force from the appliance 630 to the tooth 600. The geometry of the non-contacting surface 625 may be varied as desired (e.g., convex, concave, or planar). Further illustrated by a dotted line is alternative surface 622, which extends the convex surface 622 so that the entire exposed surface of attachment 610 would comprise a single convex surface. The attachment size and shape implied by alternative surface 622 may be too large for comfort or aesthetic reasons. Thus, it may be desirable in some embodiments to design attachments such as attachment 610 which only comprise convex surfaces where engagement with the appliance is desired, while eliminating unwanted volume where the appliance is not intended to engage the attachment so as to form non-contacting surfaces (e.g., surface 625).

In many embodiments, the appliances herein are designed to contact the convex surface of an attachment device at a single location. In alternative embodiments, an appliance can be designed to concurrently contact a single attachment device at a plurality of different locations, e.g., at 2, 3, 4, 5, or more different locations. In many embodiments, the different locations may be positioned along a single convex surface. In many embodiments, some of the different locations may be located on different sides of an attachment. In many embodiments, some of the different locations may be located on the same side of an attachment. In many embodiments, some of the different locations may be located on different convex surfaces of the attachment device. In many embodiments, one engagement portion of an appliance may contact a plurality of different locations on one or more attachment surfaces.

Figure 7A:
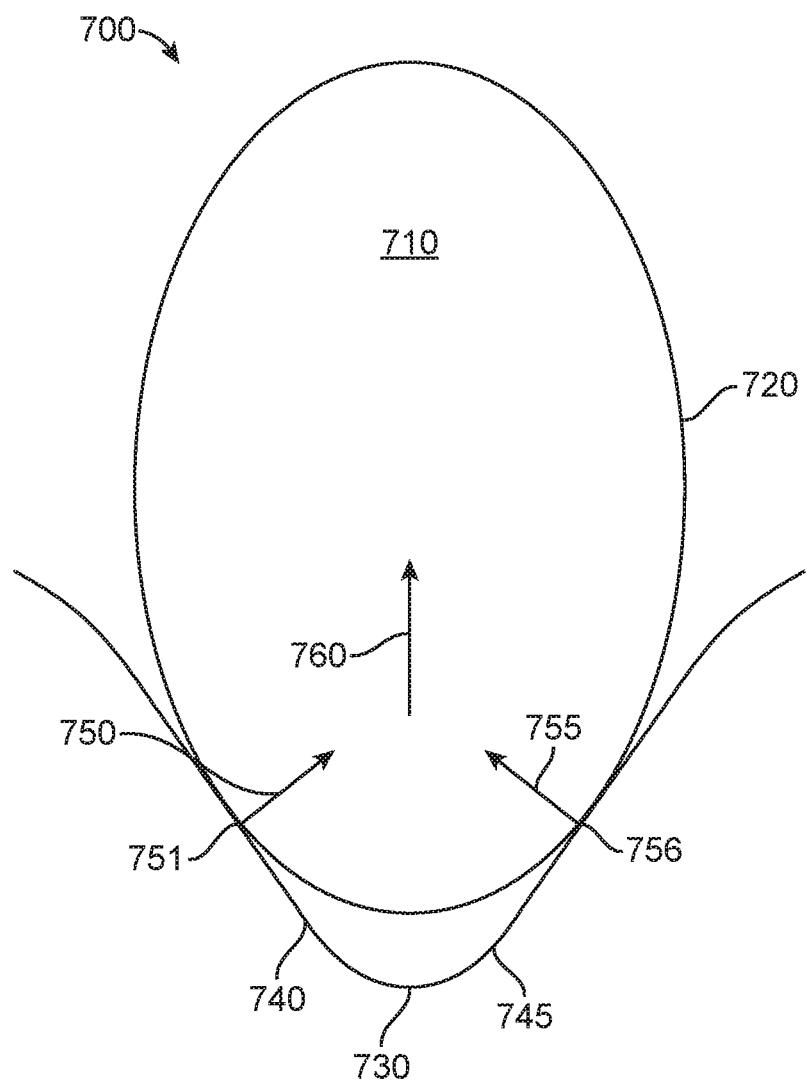
FIG. 7A illustrates an attachment with a convex surface and an appliance with a plurality of surfaces, each configured to concurrently contact the convex surface at different respective locations so as to apply a net force to a tooth, in accordance with many embodiments.

FIG. 7A illustrates an attachment with a convex surface and an appliance with a plurality of surfaces, each configured to concurrently contact the convex surface at different respective locations so as to apply a force to a tooth, in accordance with many embodiments. An attachment 710 (e.g., with an approximately ellipsoidal shape) is shown from a perspective facing toward the surface of a tooth 700, corresponding to the plane of the page. The attachment comprises a convex surface 720 configured to engage an appliance at a plurality of locations, wherein each location determines a particular force and a particular moment. In the illustrated embodiment, the attachment surface 720 is engaged by an appliance 730 with engagement portions comprising a plurality of surfaces 740 and 745. The appliance surfaces concurrently engage the convex surface 720 at separate respective contact locations 751 and 756, producing respective contact forces 750 and 755. In the depicted embodiment, these two forces add together to produce a net tooth moving force 760 pointing in an upwards direction. In alternative embodiments, the appliance may engage the attachment devices at other contact locations so as to produce forces in other directions. This configuration allows a net tooth moving force to be produced in a direction that is not substantially normal to either contacted surface. Furthermore, the different directions and locations of contact forces 750 and 755 may cause each to produce a moment on the tooth. The combination of these moments can produce a net moment which can have some components larger or smaller than those of either of the individual contacts, optionally at or near zero.

Figure 7B:
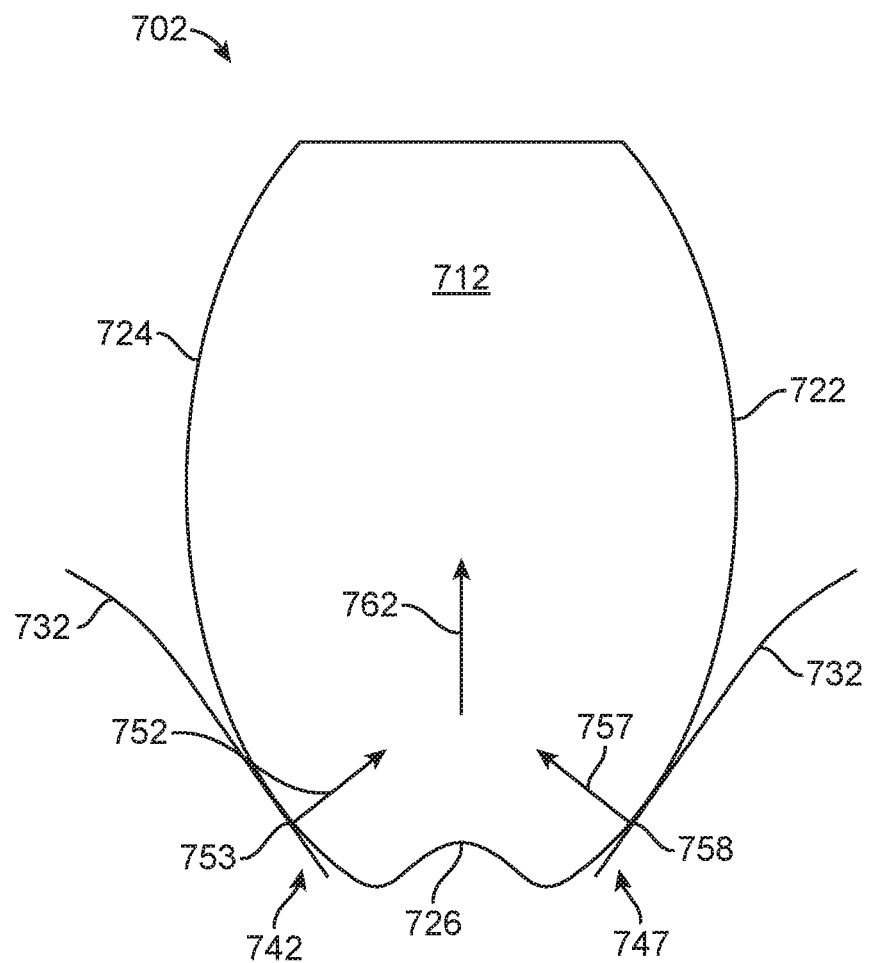
FIG. 7B illustrates an alternative configuration of the attachment and appliance of FIG. 7A, in which each appliance surface contacts a separate convex surface of the attachment, in accordance with many embodiments.

A further benefit of using more than one point of contact between appliance surfaces and convex attachment surfaces is to allow an appliance to apply tooth moving forces in directions where direct engagement with an attachment would be difficult to achieve or uncomfortable for the patient. FIG. 7B illustrates an alternative configuration of the attachment and appliance of FIG. 7A, in which each appliance surface contacts a separate convex surface of the attachment, in accordance with many embodiments. An attachment 712 with a plurality of convex attachment surfaces 722 and 724 is shown from a perspective facing toward the surface of a tooth 702, corresponding to the plane of the page. Convex surfaces 722 and 724 are configured to engage engagement portions of an appliance at a plurality of locations, wherein each location determines a particular force and a particular moment. The convex surfaces 722 and 724 are optionally separated by a non-convex surface 726, such that attachment 712 does not extend as far down from its center as attachment 710 of FIG. 7A. This feature can be useful in situations where size or shape of the attachment is constrained, for example, when an ellipsoidal attachment would extend too far towards the gum line of the patient or make an undercut shape that is difficult for a removable appliance to engage.

Each attachment surface 722 and 724 is respectively engaged by engagement portions of an appliance 732 with a plurality of respective surfaces 742 and 747. The appliance surfaces concurrently engage the respective convex surfaces 722 and 724 at separate respective contact locations 753 and 758, producing respective contact forces 752 and 757. In the depicted embodiment, these two forces add together to produce a net tooth moving force 762 pointing in an upwards direction. This configuration of appliance and attachment allows an upwards force, such as an extrusion force, to be applied to a tooth, for example, while keeping both the attachment and the appliance from extending too far towards the patient's gum line. In alternative embodiments, the appliance may engage the attachment devices at other contact locations so as to produce forces in other directions.

Figure 7C:
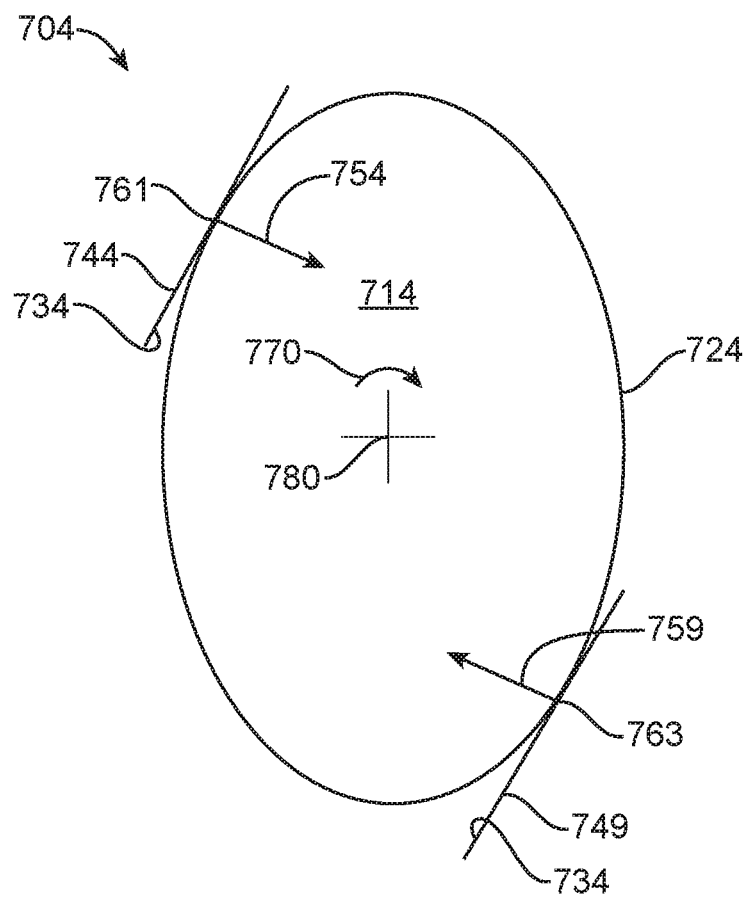
FIG. 7C illustrates an attachment with a convex surface and an appliance with a plurality of surfaces, each configured to concurrently contact the convex surface at different respective locations so as to apply a net moment to a tooth, in accordance with many embodiments.

FIG. 7C illustrates an attachment with a convex surface and an appliance with a plurality of surfaces, each configured to concurrently contact the convex surface at different respective locations so as to apply a net moment to a tooth, in accordance with many embodiments. An attachment 714 (e.g., with an approximately ellipsoidal shape) is shown from a perspective facing toward the surface of a tooth 704, corresponding to the plane of the page. The attachment comprises a convex surface 724 configured to engage an appliance at a plurality of locations, wherein each location determines a particular force and a particular moment. In the illustrated embodiment, the attachment surface 724 is engaged by an appliance 734 with engagement portions comprising a plurality of surfaces 744 and 749. The appliance surfaces concurrently engage the convex surface 724 at separate respective contact locations 761 and 763, producing respective contact forces 754 and 759. These two forces may be about equal in magnitude and approximately opposite in direction, so they produce a net force of about zero. However, due to their different contact locations 761 and 763, they produce respective moments that add together to produce a moment 770 in a clockwise direction about center of rotation 780. This configuration allows a moment to be produced by contacting a single attachment with surfaces of a single appliance without needing to apply a tooth moving force. Although the attachment is illustrated here as approximately ellipsoidal with a single convex surface similar to that of FIG. 7A, other shapes may readily be used, including shapes with separate convex surfaces such as illustrated in FIG. 7B. It will be further appreciated that the elements illustrated in FIGS. 7A-C may be freely combined; for example, to allow both a net force and a net moment to be independently determined by concurrently contacting the convex surfaces of an attachment with engagement surfaces of an appliance at one, two, or even more locations. Additionally, other forces may also be applied to the attachment or tooth in combination with those depicted in FIGS. 7A-C, e.g., to inhibit undesirable tooth movements, as would be understood by one of ordinary skill in the art.

It will be understood by one of skill in the art that in some embodiments the roles played by the attachment and the appliance may be reversed; for example, the attachment may comprise a planar surface engaged by an appliance engagement portion comprising a convex appliance surface. This reversed design allows the application of a plurality of parallel tooth-moving forces, each substantially normal to the planar attachment surface, and each arising from a different contact point. This allows a variable moment to be applied to a tooth while applying tooth moving forces that may be similar in direction and/or magnitude. Further embodiments may employ attachments that have a mix of engagement surface types—for example, some convex surfaces and some planar surfaces—in order to further customize the forces and moments that may be applied to the patient's tooth. In each case, one or more appliances may be fabricated to properly engage the respective attachment surfaces; for example, in some cases convex attachment surfaces may be engaged by planar appliance surfaces while planar attachment surfaces are engaged by convex appliance surfaces. In some cases, different attachment surface types may be engaged concurrently, in a manner similar to that depicted in FIGS. 7A and 7B, in order to provide differential moments and/or combined forces.

FIGS. 8A-8D illustrate the reduced sensitivity of attachments engaged on convex surfaces to manufacturing variations, compared to attachments engaged on planar surfaces. As described further herein, this reduced sensitivity allows a more accurate and reliable application of tooth moving force. This can allow more precise tooth movements to be performed, as well as decrease the rate at which unintended tooth movements are produced.

Figure 8B:
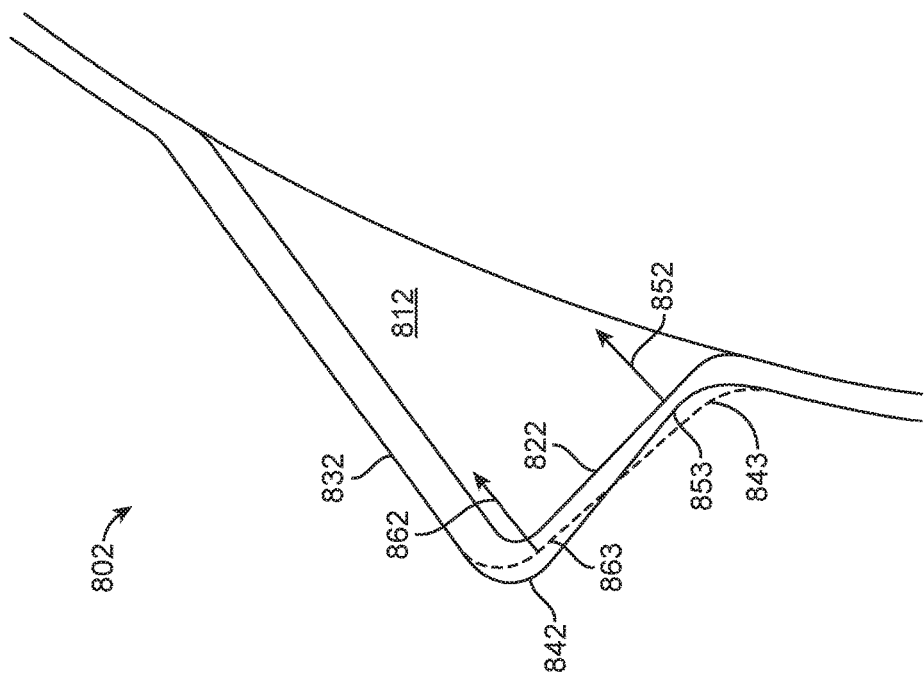
Figure 8A:
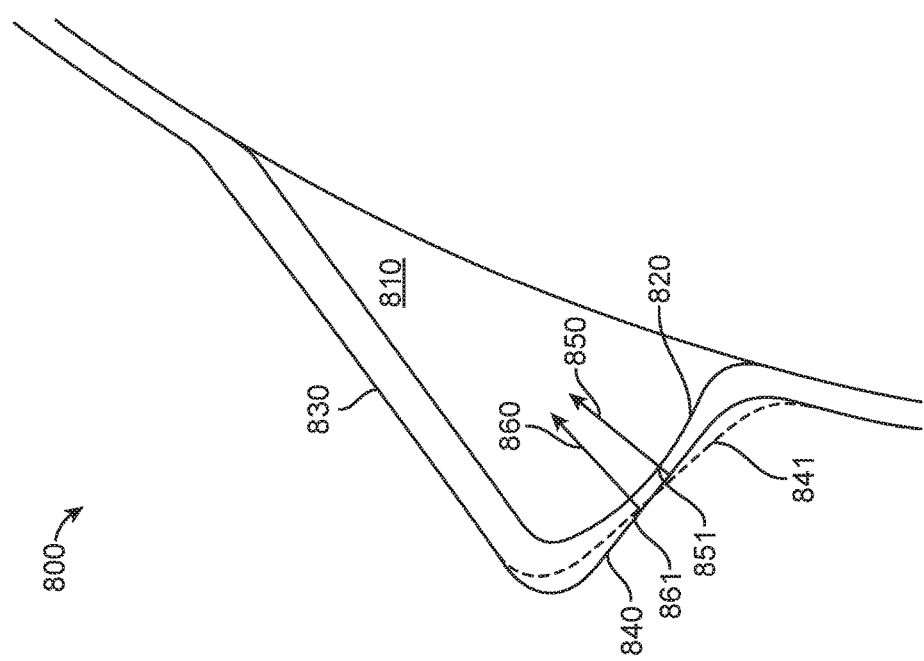

FIG. 8A illustrates the reduced sensitivity of attachments with convex surfaces to defects in appliance fabrication. An orthodontic system 800 is shown, comprising an attachment 810 with a convex surface 820 bonded to a tooth in order to allow the application of a tooth moving force when engaged by an engagement portion of an appliance 830. Orthodontic appliance 830 is illustrated with an engagement portion comprising a planar surface 840. Further illustrated is an alternate surface 841, which comprises a plane at a slightly different angle than surface 840. Due to manufacturing inaccuracies, an appliance intended to be fabricated with surface 840 might instead be fabricated with surface 841.

When surface 840 is brought into contact with attachment surface 820, it applies a force 850 at a contact location 851. By contrast, when surface 841 is brought into contact with attachment surface 820, it applies a different force 860 at a contact location 861. The difference in angles of the forces is approximately equal to the difference in angle of the planar surfaces 840 and 841. Similarly, the difference in force location is small, as can be seen by the small distance between contact locations 851 and 861. Thus, the difference in moment applied to tooth can be kept small, since the moment depends on the force and the contact location, neither of which has greatly changed.

In contrast to FIG. 8A, FIG. 8B illustrates the increased sensitivity of attachments with planar surfaces to defects in appliance fabrication. An orthodontic system 802 is shown, comprising an attachment 812 with a planar surface 822 bonded to a tooth in order to allow the application of a tooth moving force when engaged by an engagement portion an appliance 832. Orthodontic appliance 832 is illustrated with an engagement portion comprising a planar surface 842. Further illustrated is an alternate surface 843, which comprises a plane at a slightly different angle than surface 842. Due to manufacturing inaccuracies, an appliance intended to be fabricated with surface 842 might instead be fabricated with surface 843.

When surface 842 is brought into contact with attachment surface 822, it applies a force 852 at a contact location 853. By contrast, when surface 843 is brought into contact with attachment surface 822, it applies a different force 862 at a contact location 863. The difference in angles of the forces is not large, similar to the difference illustrated in FIG. 8A. However, the difference in force location is large, as can be seen by the large distance between contact locations 853 and 863. The difference in moment applied to tooth will be much larger than in corresponding FIG. 8A, since the moment depends on the force and the contact location, and the contact location has changed by a much larger amount: as illustrated, the distance between the two contact locations is nearly the full length of the planar surface 822. Thus, it can be appreciated that attachments with convex surfaces may be much less susceptible to appliance manufacturing errors than attachments with planar surfaces.

FIG. 8C illustrates the reduced sensitivity of attachments with convex surfaces to defects in attachment fabrication. An orthodontic system 804 is shown, comprising an attachment 814 with a convex surface 824 bonded to a tooth in order to allow the application of a tooth moving force when engaged by an engagement portion of an appliance 834. Orthodontic appliance 834 is illustrated with an engagement portion comprising a planar surface 844. Further illustrated is an alternate convex surface 825 of attachment 814, in which the left end of the convex surface 825 protrudes less than in convex surface 824. Due to manufacturing inaccuracies, an attachment intended to be fabricated with convex surface 824 might instead be fabricated with convex surface 825. The latter configuration of appliance and attachment is illustrated with dashed lines.

When appliance surface 844 is brought into contact with convex attachment surface 824, it applies a force 854 at a contact location 855. By contrast, when appliance surface 844 is brought into contact with attachment surface 825, it applies a different force 864 at a contact location 865. The appliance surface also translates to a different position in order to maintain contact. As can be seen in FIG. 8C, the contact location shifts a moderate amount between locations 855 and 865, due to the significant difference in shape of the convex surfaces 824 and 825, and the resulting movement of the appliance surface 844. However, despite this shift, the direction of forces 854 and 864 are substantially the same. This is because, in each case, the appliance surface is angled in the same direction, so that the force it applies—being substantially normal to the appliance surface so long as friction is low—points in substantially the same direction as well. Thus, an attachment with a convex surface can apply forces that are less sensitive to manufacturing defects of the convex surfaces.

In contrast to FIG. 8C, FIG. 8D illustrates the increased sensitivity of attachments with planar surfaces to defects in attachment fabrication. An orthodontic system 806 is shown, comprising an attachment 816 with a planar surface 826 bonded to a tooth in order to allow the application of a tooth moving force when engaged by an engagement portion of an appliance 836. Orthodontic appliance 836 is illustrated with an engagement portion comprising a planar surface 846. Further illustrated is an alternate planar surface 827 of attachment 816, in which the planar surface 827 is fabricated at a different angle than that of planar surface 826. Due to manufacturing inaccuracies, an attachment intended to be fabricated with planar surface 826 might instead be fabricated with planar surface 827. The latter configuration of appliance and attachment is illustrated with dashed lines.

When appliance surface 846 is brought into contact with planar attachment surface 826, it applies a force 856 at a contact location 857. By contrast, when appliance surface 846 is brought into contact with attachment surface 827, it applies a different force 866 at a contact location 867. The appliance surface also translates to a different position in order to maintain contact. As can be seen in FIG. 8D, the contact location shifts dramatically between locations 857 and 867, due to the difference in angle of planar surfaces 826 and 827, and the resulting movement of the appliance surface 846. Furthermore, the direction of forces 856 and 866 change as well. This can be seen from the fact that, although the appliance surface is angled in the same direction, the contact location shifts substantially, so that contact location 857 is beyond the end of planar surface 846, while contact location 867 is beyond the end of planar surface 827. Thus, in each case, the force applied may depend on the shape of the edges of the engagement portions of the appliance, rather than on the central, planar surface of the engagement portions as intended. This leads to an unpredictable force that varies strongly even with small imperfections in manufacturing. It can further be appreciated that, since both the force and the contact location change more in FIG. 8D than in corresponding FIG. 8C, the potential for variation in moment due to manufacturing defects is also greater for planar attachment surfaces than for convex surfaces.

The convex attachment devices described herein can be used in combination with a plurality of orthodontic appliances in order to produce complex tooth movement trajectories that involve sequential application of forces along different directions and/or at different locations. For example, the tooth movement trajectories may be non-linear trajectories, such as curved trajectories or trajectories with a variable tooth movement velocity (e.g., accelerating or decelerating movements). Some trajectories may comprise "round-tripping" motion, in which a tooth is moved in one direction away from an initial position and/or orientation, then later in an opposing direction at least partially towards to the initial position and/or orientation. Round-tripping may be beneficial, for example, to move an obstructing tooth away from the path of another tooth. In some cases, a tooth may be moved in a substantially straight line despite applying forces at different angles, because the applied forces act to oppose other forces incident on the tooth. In some cases, a portion of a trajectory may involve no motion of a tooth; for example, to allow other teeth to move in the meantime. Two or more sequential trajectories, whether complex or simple, may be combined to form an overall trajectory, which may be complex. Such combination may be repeated as desired to make an arbitrarily complex trajectory.

FIGS. 9A-9E illustrate how a tooth may be moved in a complex trajectory while applying forces to a single attachment comprising one or more convex surfaces, in accordance with embodiments.

FIG. 9A illustrates a tooth 900 bonded to an attachment 910 with a convex surface. In the depicted embodiment, the tooth 900 is desired to move to a target location 990, but cannot travel in a straight line because an obstructing tooth 905 is partially in the way. For this reason, a curved trajectory 980 is planned to move tooth 900 from its starting position to its target location 990. The first step is accomplished by fabricating an appliance with an engagement portion comprising a surface that engages the attachment's convex surface at a contact location 951 on the left side of the attachment, applying a force 950 pushing the tooth in a distal direction, toward the right of the image.

FIG. 9B shows the tooth 900 as it first begins moving. A first appliance contacts the attachment 910 at a contact location 953 chosen to produce a tooth moving force 952 that continues to push the tooth distally.

FIG. 9C illustrates the tooth 900 farther along its trajectory. Now that the tooth 900 is mostly clear of the obstructing tooth 905, the angle of force 954 is shifted by fabricating a second appliance to contact to contact the attachment 910 at a point 955 so as to apply a force pointed more toward the lingual direction at the top of the page.

FIG. 9D illustrates the tooth 900 after fully clearing the obstructing tooth 905. The tooth 900 no longer needs to move distally, so a third appliance is fabricated with an engagement portion with a surface to contact the convex surface of attachment 910 at a point 957, thereby applying a force 956 in a lingual direction.

FIG. 9E shows the tooth 900 after arriving at its target location, in the desired alignment with tooth 905. At this point, orthodontic treatment may stop and attachment 910 may be removed. Alternately, if further movement of tooth 900 is desired (for example, extrusion, intrusion, translation, or rotation), then additional appliances may be fabricated with engagement portions comprising one or more surfaces configured to contact attachment 910 at the appropriate points to apply the required tooth moving forces.

FIGS. 10A-10E illustrate the use of an attachment comprising one or more convex surfaces to rotate a tooth in multiple directions to provide space to move a second tooth, thereby allowing a complex reorganization of teeth, in accordance with embodiments.

FIG. 10A illustrates a configuration of teeth in which a first tooth 1005 is desired to move to a target location 1090. In the depicted embodiment, a second tooth 1000 obstructs the straight line path. In order to rearrange the teeth to the desired configuration, the first tooth 1005 may be moved along a curved trajectory 1080, while the second tooth 1000 may be sequentially rotated: first with a clockwise rotation 1082, then with a counterclockwise rotation 1084 to return it to its original orientation.

FIG. 10B illustrates the starting position, in which a rotational movement is caused to the second tooth 1000 by applying a force 1050 to an attachment 1010 with a convex surface by engaging that surface with a first appliance at a contact location 1051. This produces a moment 1070 on the tooth 1000, causing a rotation of the tooth in a clockwise direction. Optionally, other forces (not shown) may also be applied to inhibit any translational movements elicited by the force 1050.

FIG. 10C illustrates a new tooth configuration in which the second tooth 1000 has been rotated to a position where it no longer obstructs the first tooth 1005. The first tooth 1005 is then moved along a trajectory 1080 to its target location. This movement may be accomplished using attachments with convex surfaces, as described in detail in FIGS. 9A-E, or by other methods; for example, using one or more conventional attachments, using appliances acting directly on tooth 1000, etc.

FIG. 10D illustrates the configuration of teeth 1000 and 1005 after the first tooth 1005 has arrived at its target location. The second tooth 1000 is now to be rotated to its original orientation, which requires a counterclockwise rotation. Accordingly, a second appliance is fabricated with an engagement portion with a surface configured to contact attachment 1010 at location 1053, thereby applying a force 1052 in the rightwards direction. This force produces a moment 1072 that causes a rotation of tooth 1000 in a counterclockwise direction. Optionally, other forces (not shown) may also be applied to inhibit any translational movements elicited by the force 1052.

FIG. 10E illustrates the final configuration of teeth 1000 and 1005 with each tooth in its desired location and orientation. At this point, orthodontic treatment may stop and attachment 1010 may be removed. Alternately, if further movement of tooth 1000 or tooth 1005 is desired (for example, extrusion, intrusion, translation, or rotation), then appliances may be fabricated with one or more engagement portions comprising one or more surfaces configured to contact attachment 1010 (or a corresponding attachment on tooth 1005) at the appropriate points to apply the required tooth moving forces.

Figure 11:
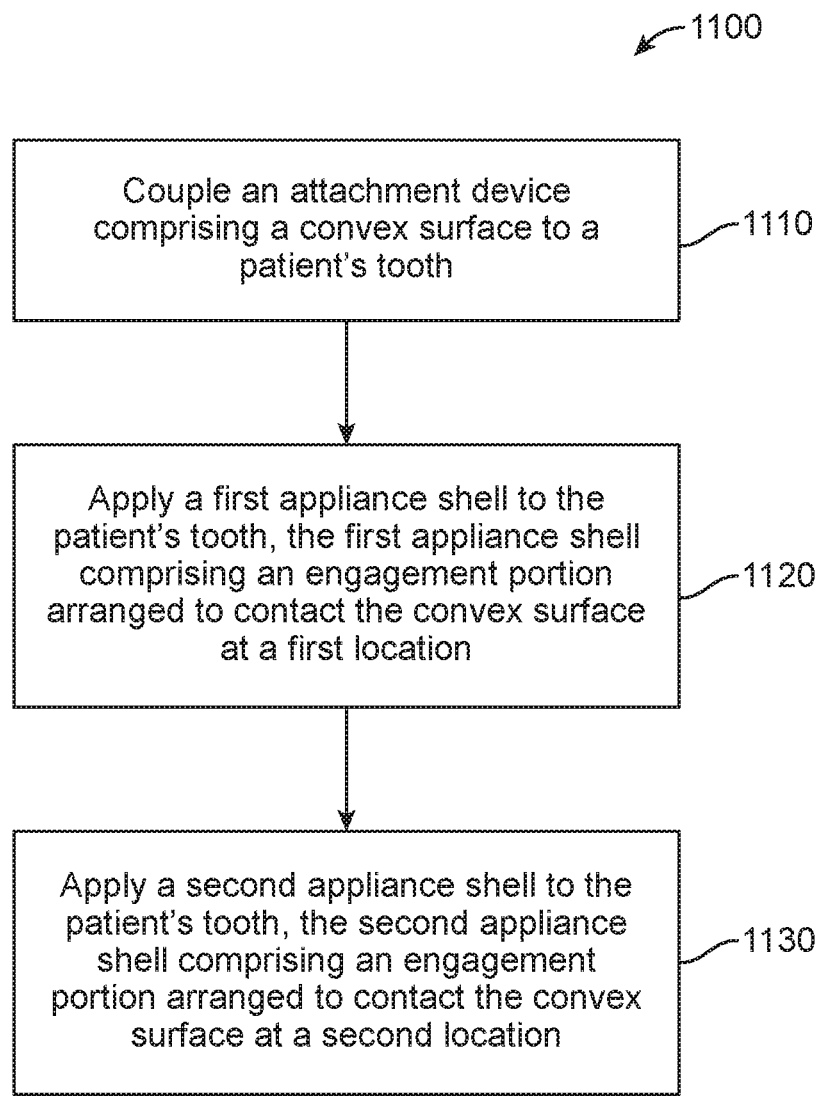
FIG. 11 illustrates a method of treating a patient using an attachment comprising a convex surface and one or more appliances, in accordance with many embodiments.

FIG. 11 illustrates a method 1100 of treating a patient using an attachment comprising a convex surface and one or more appliances, in accordance with embodiments. The method 1100, as with all other methods herein, can be used in combination with any embodiment of the attachment devices and appliances provided herein.

In step 1110, an attachment device comprising a convex surface is coupled to a patient's tooth. The attachment device may be mounted on the tooth by bonding the device to a surface of a tooth, using adhesive, for example. Alternatively, attachment may be molded and cured in situ, e.g., using a template appliance having an appropriately shaped recess to define the shape of the attachment. The position, orientation, and surface geometry of the attachment device may be chosen so as to allow the application of desired tooth moving forces by one or more appliances.

In step 1120, an appliance is supplied to the patient for placement in the patient's mouth. The shell of the appliance comprises an engagement portion arranged to contact the convex surface at a first location, thereby applying a tooth moving force at that location, and in a direction that is substantially normal to the surface of the attachment at the first location. This tooth moving force may cause a movement of the tooth along a desired trajectory. In some cases, the desired trajectory may be that the tooth be prevented from moving, in which case the tooth moving force may be applied to counteract an otherwise expected movement. Additionally or alternatively, the tooth moving force may be applied to reduce, prevent, or reverse a movement in a particular direction, while allowing or causing movement in another direction.

In step 1130, a second appliance is supplied to the patient for placement in the patient's mouth. The shell of the appliance comprises an engagement portion arranged to contact the convex surface at a first location, thereby applying a tooth moving force at that location, and in a direction that is substantially normal to the surface of the attachment at the first location. This tooth moving force may cause a movement of the tooth along a desired trajectory. In some cases, the desired trajectory may be that the tooth be prevented from moving, in which case the tooth moving force may be applied to counteract an otherwise expected movement. Additionally or alternatively, the tooth moving force may be applied to reduce, prevent, or reverse a movement in a particular direction, while allowing or causing movement in another direction.

Step 1130 is optional, and may be omitted. For example, step 1130 may be unnecessary if step 1120 was sufficient to arrange the patient's teeth as desired. Step 1130 may also be unnecessary if orthodontic correction after step 1120 is to be performed without orthodontic appliances or without use of the convex-surfaced attachment. Alternatively, step 1130 may be repeated as many times as needed, applying to the patient's tooth a third appliance, fourth appliance, fifth appliance, and so on to accomplish long and/or complex movements of teeth.

Figure 12:
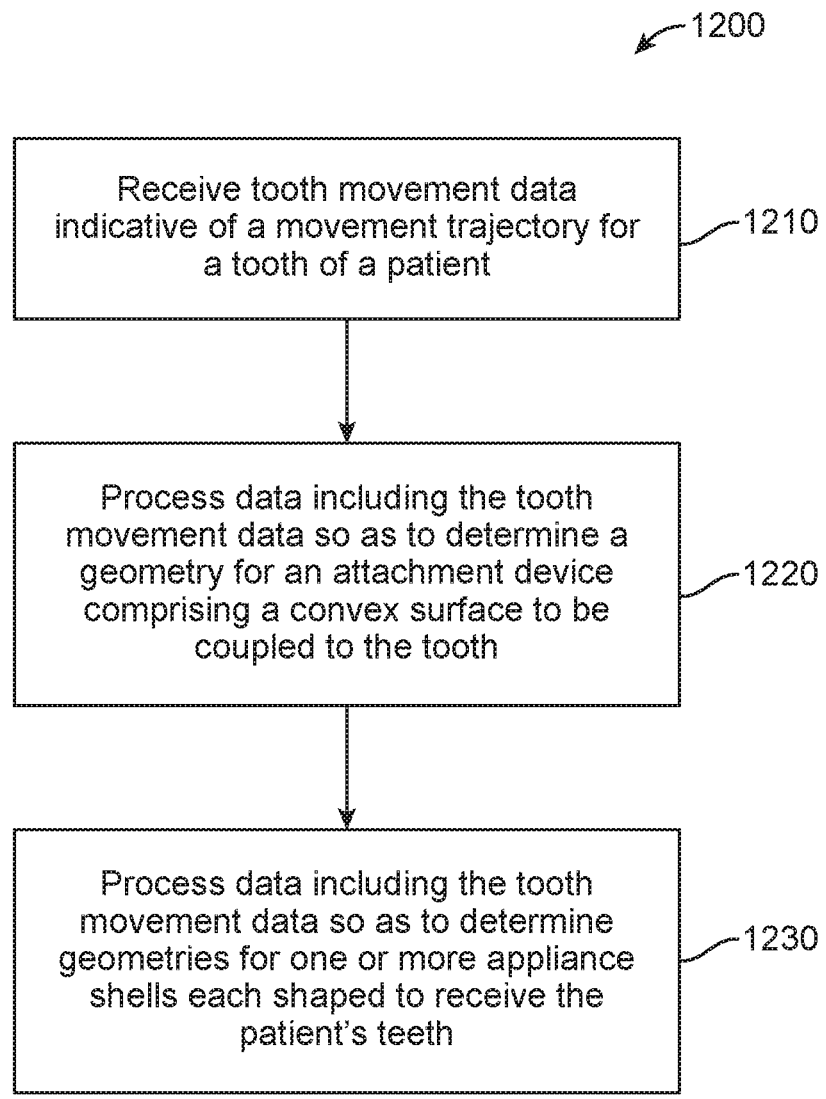
FIG. 12 illustrates a method of designing appliances and attachments to treat a patient, in accordance with many embodiments.

FIG. 12 illustrates a method 1200 of designing appliances and attachments to treat a patient, in accordance with embodiments. Method 1200 may be performed by a data processing system, as disclosed herein.

In step 1210, tooth movement data are received indicative of a tooth movement trajectory for a tooth of a patient. The tooth movement data may comprise a starting position and target position of one or more teeth, as well as trajectories over which the one or more teeth are desired to be moved. The positions of further teeth not desired to be moved may also be specified. The indicated movement trajectories may comprise an ordered sequence of movements, and different teeth may be moved concurrently or sequentially as part of the overall movement trajectory of the teeth. In some embodiments, the movement paths are configured to move the teeth in the quickest fashion with the least amount of round-tripping to bring the teeth from their initial positions to their desired target positions. Alternatively, some round tripping may be used; for example, to allow other aspects of the movement paths to be easier to perform. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 1220, the system processes data including the tooth movement data so as to determine a geometry for an attachment device comprising a convex surface to be coupled to the tooth. To determine the geometry of the attachment device, a force system to produce movement of the one or more teeth along the movement path may be determined. A force system can include one or more forces and/or one or more moments. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Based on the set of forces and/or moments identified to cause the tooth movement, an attachment geometry may be determined. The attachment geometry may include an attachment surface shape as well as an attachment position and orientation of the surface of a tooth. In some cases, a plurality of attachments may be chosen for attachment to one or more teeth. The attachment surface shape may be chosen to allow forces to be applied by one or more appliance surfaces contacting the attachment at one or more respective locations. For example, an attachment may be designed with one or more convex surfaces, wherein for each force and/or moment to be applied to the attachment, that force and/or moment may be applied by contacting an appliance surface to the attachment at one or more locations on one or more of its convex surfaces. In some cases, the choice of attachment surface shape may be made by choosing from a set of pre-designed surfaces, such as spherical, ellipsoidal, or cylindrical surface portions. In further cases, the attachment surface shape may be custom designed based on the set of forces and/or moments desired; for example, a convex surface may be designed by identifying a solid angle large enough to include all desired forces, then choosing a convex surface large enough to include at least the identified solid angle.

In step 1230, the system processes data including the tooth movement data so as to determine geometries for one or more appliance shells shaped to fit the patient's teeth. The appliance shells may comprise engagement portions with surfaces configured to engage one or more convex surfaces of the attachments identified in step 1220 at locations chosen to apply the desired forces and/or moments needed to cause the tooth movements along the trajectory identified in step 1210. In some cases, an appliance may comprise a plurality of surfaces to engage one or more convex surfaces of an attachment, so as to produce combined or differential forces and/or moments. In cases involving a plurality of appliance shells, each shell may have independently configured engagement portions with respective independently configured surfaces, allowing each shell to apply an independently chosen force and/or moment by engaging one or more convex attachment surfaces at independently determined locations. By applying these appliances sequentially to the patient's teeth, a sequence of tooth movements may be caused, the net effect of which is to move one or more teeth along controlled trajectories over time. Each appliance may be designed to properly receive the patient's teeth in the positions they are expected to be in at the time the appliance is to be worn, and these designs may be updated over time, for example, if further measurements of the patient's teeth indicate that one or more teeth are not moving as predicted.

Figure 13:
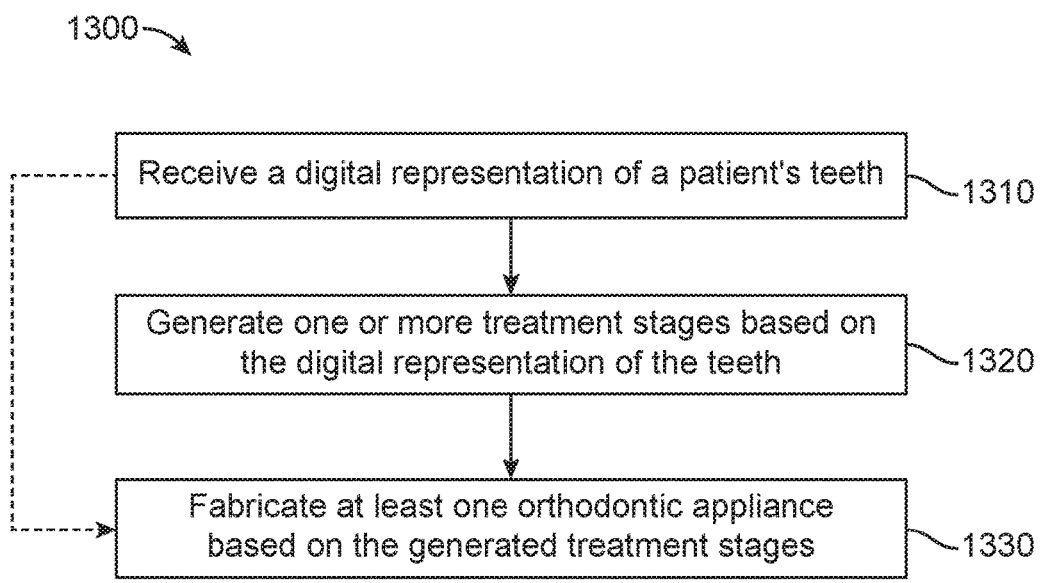
FIG. 13 illustrates a method for digitally planning an orthodontic treatment, in accordance with many embodiments.

FIG. 13 illustrates a method for digitally planning an orthodontic treatment, in accordance with embodiments. The method 1300 can be applied to any of the treatment procedures described herein and can be performed by any suitable data processing system. Any embodiment of the appliances or attachments described herein can be designed or fabricated using the method 1300.

In step 1310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 1320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 1330, at least one orthodontic appliance is fabricated based on the generated treatment stages. For example, a set of appliances can be fabricated to be sequentially worn by the patient to incrementally reposition the teeth from the initial arrangement to the target arrangement. Some of the appliances can be shaped to accommodate a tooth arrangement specified by one of the treatment stages. Alternatively or in combination, some of the appliances can be shaped to accommodate a tooth arrangement that is different from the target arrangement for the corresponding treatment stage. For example, as previously described herein, an appliance may have a geometry comprising an engagement portion with a surface to engage a particular location of a convex surface of an attachment bonded to a patient's tooth, so as to apply a desired force and/or moment to the tooth. Such an appliance may be used to ensure that a suitable amount of force is expressed on the teeth as they approach or attain their desired target positions for the treatment stage. As another example, an appliance can be designed in order to apply a specified force system on the teeth and may not have a geometry corresponding to any current or planned arrangement of the patient's teeth.

In some instances, staging of various arrangements or treatment stages may not be necessary for design and/or fabrication of an appliance. As illustrated by the dashed line in FIG. 13, design and/or fabrication of an orthodontic appliance, and perhaps a particular orthodontic treatment, may include use of a representation of the patient's teeth (e.g., receive a digital representation of the patient's teeth 1310), followed by design and/or fabrication of an orthodontic appliance based on a representation of the patient's teeth in the arrangement represented by the received representation.

Figure 14:
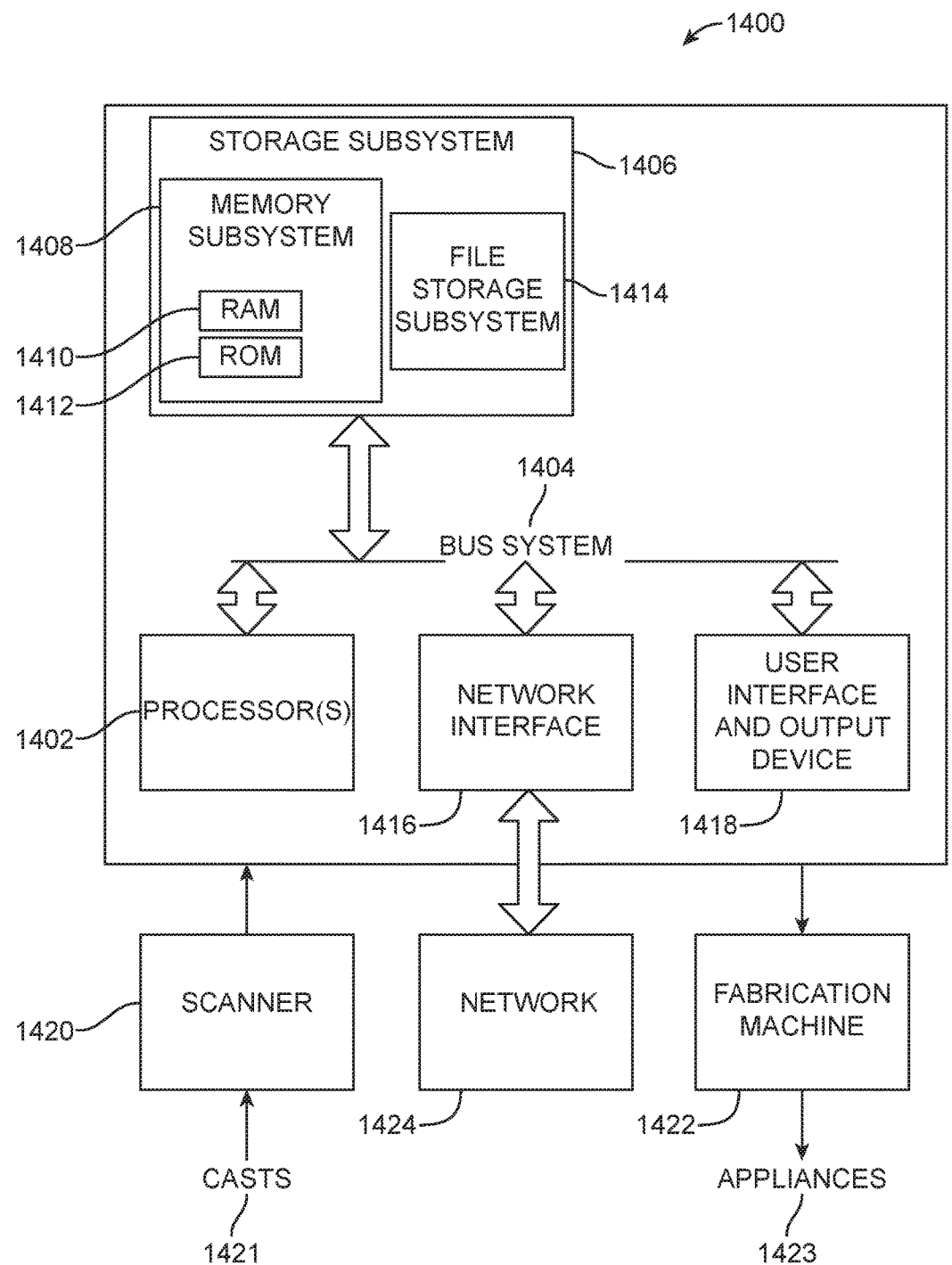
FIG. 14 is a simplified block diagram of a data processing system, in accordance with many embodiments.

FIG. 14 is a simplified block diagram of a data processing system 1400 that may be used in executing methods and processes described herein. The data processing system 1400 typically includes at least one processor 1402 that communicates with one or more peripheral devices via bus subsystem 1404. These peripheral devices typically include a storage subsystem 1406 (memory subsystem 1408 and file storage subsystem 1414), a set of user interface input and output devices 1418, and an interface to outside networks 1416. This interface is shown schematically as "Network Interface" block 1416, and is coupled to corresponding interface devices in other data processing systems via communication network interface 1424. Data processing system 1400 can include, for example, one or more computers, such as a personal computer, workstation, mainframe, laptop, and the like.

The user interface input devices 1418 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1406 maintains the basic required programming, including computer readable media having instructions (e.g., operating instructions, etc.), and data constructs. The program modules discussed herein are typically stored in storage subsystem 1406. Storage subsystem 1406 typically includes memory subsystem 1408 and file storage subsystem 1414. Memory subsystem 1408 typically includes a number of memories (e.g., RAM 1410, ROM 1412, etc.) including computer readable memory for storage of fixed instructions, instructions and data during program execution, basic input/output system, etc. File storage subsystem 1414 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1420 includes any means for obtaining a digital representation (e.g., images, surface topography data, etc.) of a patient's teeth (e.g., by scanning physical models of the teeth such as casts 1421, by scanning impressions taken of the teeth, or by directly scanning the intraoral cavity), which can be obtained either from the patient or from treating professional, such as an orthodontist, and includes means of providing the digital representation to data processing system 1400 for further processing. Scanner 1420 may be located at a location remote with respect to other components of the system and can communicate image data and/or information to data processing system 1400, for example, via a network interface 1424. Fabrication system 1422 fabricates appliances 1423 based on a treatment plan, including data set information received from data processing system 1400. Fabrication machine 1422 can, for example, be located at a remote location and receive data set information from data processing system 1400 via network interface 1424.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. An orthodontic system for repositioning a patient's teeth, the system comprising:
    an attachment device configured to be coupled to a tooth of the patient and comprising a convex surface having a radius of curvature of at least 10mm; and
    a plurality of appliance shells each including a plurality of tooth receiving cavities shaped to receive the patient's teeth and at least one of the plurality of appliances comprising a receptacle extending from one of the plurality of tooth receiving cavities, the receptacle having a planar engagement portion positioned to engage the convex surface of the attachment device so as to apply a repositioning force to the tooth,
    wherein the engagement portions of at least some of the plurality of appliance shells are each arranged to contact the convex surface at a different respective location so as to apply different respective repositioning forces to the tooth.

2. The system of claim 1, wherein the attachment device comprises a single convex surface.

3. The system of claim 2, wherein the convex surface comprises a spherical, ellipsoidal, or cylindrical shape profile.

4. The system of claim 1, wherein the planar surfaces of the at least some of the plurality of appliance shells are each arranged at different orientations relative to the convex surface.

5. The system of claim 1, wherein at least some of the plurality of appliance shells are each arranged to contact the convex surface at a different respective orientations.

6. The system of claim 1, wherein the different respective locations are configured to reposition the tooth along a non-linear movement trajectory.

7. The system of claim 1, wherein each engagement portion is positioned so as to contact the convex surface of the attachment device at a single location.

8. The system of claim 1, wherein at least one of the plurality of appliance shells comprises a plurality of engagement portions positioned to contact the convex surface at a plurality of different locations.

9. The system of claim 1, wherein the attachment device further comprises a non-contacting surface that does not engage the plurality of appliance shells.

10. An orthodontic appliance for repositioning a patient's teeth, the appliance comprising:
    an attachment device configured to be coupled to a tooth of the patient and comprising a convex surface having a radius of curvature of at least 10mm; and
    a shell comprising a plurality of cavities shaped to receive the patient's teeth, wherein at least one cavity of the plurality of cavities comprises a receptacle extending from the at least one cavity and being shaped to receive the attachment device, the receptacle comprising a planar surface positioned to engage the convex surface of the attachment device at a single location so as to apply a repositioning force to the tooth.

* * * * *